US009809781B1

(12) United States Patent
Maddi et al.

(10) Patent No.: US 9,809,781 B1
(45) Date of Patent: *Nov. 7, 2017

(54) THERMAL FRACTIONATION OF BIOMASS OF NON-LIGNOCELLULOSIC ORIGIN FOR MULTIPLE HIGH-QUALITY BIOFUELS

(71) Applicant: The University of Toledo, Toledo, OH (US)

(72) Inventors: Balakrishna Maddi, Toledo, OH (US); Sridhar Viamajala, Toledo, OH (US); Sasidhar Varanasi, Toledo, OH (US)

(73) Assignee: The University of Toledo, Toledo, OH (US)

( * ) Notice: Subject to any disclaimer, the term of this patent is extended or adjusted under 35 U.S.C. 154(b) by 369 days.

This patent is subject to a terminal disclaimer.

(21) Appl. No.: 14/589,405

(22) Filed: Jan. 5, 2015

Related U.S. Application Data

(63) Continuation-in-part of application No. 13/294,510, filed on Nov. 11, 2011, now Pat. No. 8,927,240.

(60) Provisional application No. 61/413,177, filed on Nov. 12, 2010.

(51) Int. Cl.
*C11B 1/10* (2006.01)
*C08B 31/00* (2006.01)
*C07K 14/405* (2006.01)
*C10L 1/02* (2006.01)
*C07K 1/14* (2006.01)

(52) U.S. Cl.
CPC ............... *C11B 1/10* (2013.01); *C07K 1/145* (2013.01); *C07K 14/405* (2013.01); *C08B 31/00* (2013.01); *C10L 1/026* (2013.01); *C10L 2200/0476* (2013.01)

(58) Field of Classification Search
None
See application file for complete search history.

(56) References Cited

PUBLICATIONS

Ross AB et al. Investigation of the pyrolysis behaviour of brown algae before and after pretreatment using PY-GC/MS and TGA. 2009. Journal of Analytical and Applied Pyrolysis. 85:3-10.*

* cited by examiner

*Primary Examiner* — Paul Holland
(74) *Attorney, Agent, or Firm* — MacMillan, Sobanski & Todd, LLC

(57) ABSTRACT

Methods for production of multiple biofuels through thermal fractionation of biomass feedstocks are described. The products of said methods are also described.

19 Claims, 34 Drawing Sheets
(21 of 34 Drawing Sheet(s) Filed in Color)

| Retention time | Compound | Confidence |
|---|---|---|
| 1.96 | 3-buten-2-ol | 625 |
| 2.29 | 2-Propanone, 1-hydroxy | 864 |
| 3.78 | 3-amino-2-oxazolidinone | 695 |
| 4.00 | Propanenitrile, 3-butoxy | 687 |
| 4.83 | Furfural | 799 |
| 5.52 | 2-furanmethanol | 879 |
| 7.77 | 2(5H)-furanone | 714 |
| 8.00 | 2-furancarboxaldehyde, 5-methyl | 803 |
| 8.34 | 2-cyclopenten-1-one, 2-hydroxy | 893 |
| 9.61 | 2,3-pentanedione | 660 |
| 9.70 | 2-Butanone, 1-(acetyloxy) | 808 |
| 10.18 | 4(1H)-Pyrimidinone, 6-methyl | 646 |
| 11.24 | 1,2-Cyclopentanedione, 3-methyl | 796 |
| 11.71 | 1-amino-2,6-dimethylpiperidine | 648 |
| 12.57 | 2,5-dimethyl-4-hydroxy-3(2H)-furanone | 770 |
| 12.80 | Cyclopropyl carbinol | 752 |
| 13.10 | Maltol | 716 |
| 14.21 | 1,4-dioxane-2,5-dione,3,6-dimethyl | 763 |
| 14.58 | Metyl isobutyl ketone | 668 |
| 14.68 | 1,4:3,6-dianhydro-alpha-d-glucopyranose | 661 |
| 15.17 | 3,4-anhydro-d-galactosan | 651 |
| 16.19 | Indole | 714 |
| 19.05 | Beta-D-glucopyranose | 824 |
| 19.74 | Dodecanoic acid | 639 |
| 21.4 | Heptadecane | 735 |
| 22.04 | Tetradecanoic acid | 628 |
| 23.34 | 3,7,11,15-tetramethyl-2-hexadecen-1-ol | 714 |
| 24.23 | Hexadecanoic acid | 904 |
| 25.83 | 9,12-octadecadienoic acid | 797 |
| 25.91 | 9-octadecenoic acid | 793 |
| 26.10 | Octadecanoic acid | 790 |

FIG. 7 – Table 1

| Retention time | Compound | Confidence |
|---|---|---|
| 1.93 | Acetic acid | 617 |
| 2.34 | 2-propanone, 1-hydroxy | 865 |
| 3.40 | Acetic acid anhydride | 630 |
| 3.73 | 3-Amino-2-oxazolidinone | 716 |
| 5.53 | 2-furanmethanol | 901 |
| 7.87 | 2(5H) Furanone | 772 |
| 8.41 | 2-Cyclopenten-1-one, 2-hydroxy | 830 |
| 12.48 | 3-furancarboxylic acid, methyl ester | 820 |
| 12.82 | Cyclopropyl carbinol | 771 |
| 13.97 | 1,4-dioxaspiro[2.4]hepta-5-one, 7-methyl | 666 |
| 14.10 | 1,3-dioxolane-4-methanol | 623 |
| 14.25 | Undecanoic acid | 644 |
| 14.96 | 1,4:3,6-dianhydro-alpha-d-glucopyranose | 735 |
| 15.15 | 2-furancarboxaldehyde, 5-(hydroxymethyl) | 712 |
| 15.78 | Nonanoic acid | 673 |
| 19.02 | Beta-d-glucopyranose, 1,6-anhydro | 739 |
| 19.73 | Dodecanoic acid | 634 |
| 21.41 | Heptadecane | 822 |
| 22.90 | 3,7,11,15-tetramethyl-2-hexadecen-1-ol | 661 |
| 24.25 | Hexadecanoic acid | 842 |
| 25.91 | Oleic acid | 818 |
| 26.11 | Octadecanoic acid | 793 |
| 30.48 | 1-docosene | 689 |

FIG. 8 – Table 2

| Retention time | Compound | Confidence |
|---|---|---|
| 1.92 | 1-Hexene | 750 |
| 2.48 | 2,3-dimethyl pentane | 761 |
| 3.40 | Toluene | 854 |
| 3.80 | 2-octene | 780 |
| 4.00 | Octane | 863 |
| 7.50 | Nonane | 786 |
| 10.50 | Hexanoic acid | 714 |
| 10.60 | Decane | 659 |
| 12.34 | Phenol, 3-methyl | 749 |
| 12.68 | Heptanoic acid | 742 |
| 12.90 | Undecane | 833 |
| 13.0 | 2-Undecene | 716 |
| 14.00 | Benzene, pentyl | 658 |
| 14.40 | Octanoic acid | 829 |
| 15.90 | Nonanoic acid | 779 |
| 16.15 | 1-Tridecene | 755 |
| 16.30 | Tridecane | 768 |
| 17.26 | Decanoic acid | 725 |
| 17.58 | 1-Tetradecanol | 740 |
| 17.70 | Tetradecane | 813 |
| 19.0 | Pentadecane | 881 |
| 19.74 | Dodecanoic acid | 639 |
| 21.16 | 8-Heptadecene | 823 |
| 21.4 | Heptadecane | 735 |
| 22.04 | Tetradecanoic acid | 712 |
| 23.58 | Hexadecanenitrile | 705 |
| 24.43 | Hexadecanoic acid | 886 |
| 24.89 | Heptadecanoic acid | 844 |
| 25.31 | Octadecanoic acid,2-propenyl ester | 714 |
| 26.10 | 9-octadecenoic acid | 887 |
| 26.26 | Octadecanoic acid | 856 |
| 26.90 | Erucic acid | 679 |

FIG. 14 – Table 3

| Ret. Time | Compound | confidence |
|---|---|---|
| 2.49 | 3-methyl Hexane | 757 |
| 3.40 | Toluene | 784 |
| 19.0 | Pentadecane | 813 |
| 19.74 | Dodecanoic acid | 639 |
| 21.16 | 8-Heptadecene | 778 |
| 21.4 | Heptadecane | 663 |
| 22.04 | Tetradecanoic acid | 712 |
| 23.98 | 9-hexadecenoic acid | 792 |
| 24.26 | Hexadecanoic acid | 881 |
| 25.31 | Octadecanoic acid,2-propenyl ester | 632 |
| 26.00 | 9-octadecenoic acid | 889 |
| 26.16 | Octadecanoic acid | 840 |
| 26.90 | Erucic acid | 679 |

FIG. 15 – Table 4

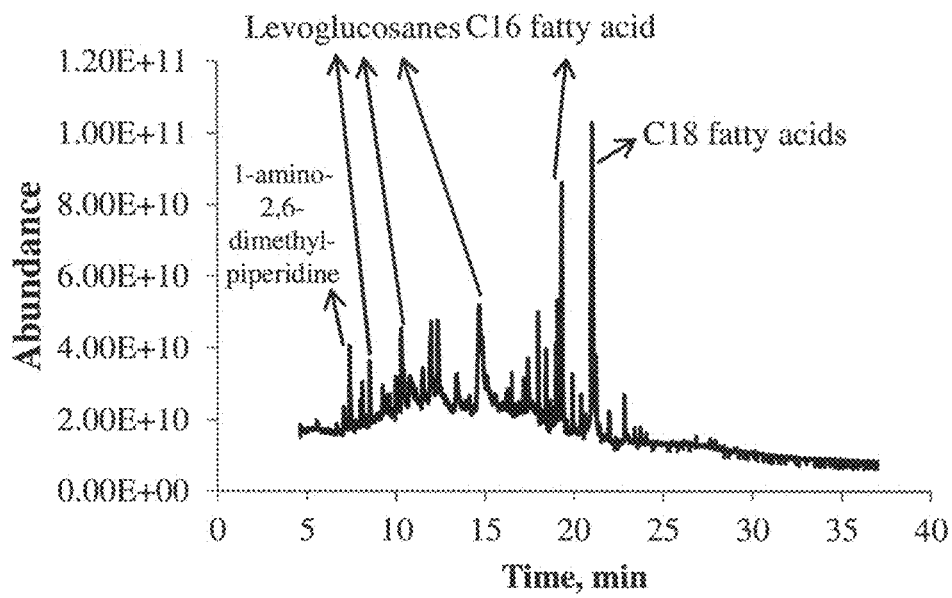

FIG. 17

| Retention time | Compound | Confidence |
|---|---|---|
| 6.70 | Methamphetamine, propionyl | 607 |
| 7.10 | 1,2-cyclopentanedione, 3-methyl | 763 |
| 7.44 | 1-amino-2,6-dimethylpiperidine | 625 |
| 8.01 | Hexanoic acid, 2-propenyl ester | 666 |
| 8.12 | 2,5-dimethyl-4-hydroxy-3(2H)furanone | 731 |
| 8.54 | Levoglucosenone | 849 |
| 9.63 | Pentanoic acid, methyl ester | 643 |
| 10.31 | 1,4:3,6-dianhydro-alpha-d-glucopyranose | 773 |
| 10.83 | 4-pyridinol | 609 |
| 11.51 | 2-butenedioic acid, 2-methyl | 661 |
| 12.38 | Alpha-D-glucopyranoside, methyl | 674 |
| 14.69 | Beta-D-glucopyranose, 1,6-anhydro | 731 |

FIG. 18 – Table 5

| Mass | Stream number | | | Summative Mass closure |
|---|---|---|---|---|
| | 2a | 2b | 2d | |
| Total mass (g) | 5.16 | 1.63 | 2.04 | 71% |
| Lipid and lipid derivatives (g) | 1.65† | 1.55‡ | 0.0 | 94% |
| Nitrogen (g) | 0.14 | 0.03 | 0.09 | 86% |

| Retention time | Compound | Confidence |
|---|---|---|
| 6.2 | Pentanoic acid | 804 |
| 7.6 | Butyl-benzene | 759 |
| 7.95 | Heptanoic acid | 683 |
| 8.15 | 1-decene | 752 |
| 8.3 | Undecane | 859 |
| 8.40 | 4-undecene | 835 |
| 8.58 | 5-undecene | 748 |
| 8.76 | Cyclodecene | 704 |
| 9.3 | Pentyl-benzene | 696 |
| 9.52 | Octanoic acid | 802 |
| 9.80 | 3-dodecene | 759 |
| 9.92 | Dodecane | 826 |
| 10.12 | Undecane, 2,6-dimethyl | 766 |
| 10.32 | Cyclododecene | 820 |
| 10.86 | Hexyl benzene | 690 |
| 10.97 | Nonanoic acid | 827 |
| 11.10 | Octanoic acid, 2-propenyl ester | 702 |
| 11.30 | 1-tridecene | 840 |
| 11.41 | Tridecane | 818 |
| 12.37 | Decanoic acid | 758 |
| 12.70 | 1-tetradecene | 869 |
| 12.81 | Tetradecane | 797 |
| 13.50 | Cyclopentane, nonyl | 808 |
| 13.63 | Undecanoic acid | 812 |
| 14.02 | 1-pentadecene | 864 |
| 14.12 | Pentadecane | 666 |
| 14.84 | Nonylcyclohexane | 815 |
| 14.90 | Pentadecane, 2-methyl | 757 |
| 15.17 | 1-hexadecene | 850 |
| 15.26 | 1-hexadecene | 821 |
| 15.30 | Hexadecane | 871 |
| 16.18 | 6,9-heptadecadiene | 765 |
| 16.27 | 8-heptadecene | 723 |
| 16.52 | Heptadecane | 680 |
| 16.62 | Benzene, 1-methyldecyl | 707 |
| 17.20 | 2-hexadecenoic acid | 649 |
| 18.70 | Hexadecanenitrile | 814 |
| 19.40 | Hexadecanoic acid | 671 |
| 20.00 | Heptadecanoic acid | 788 |
| 20.52 | Oleanitrile | 739 |
| 21.11 | Oleic acid | 788 |
| 21.33 | Octadecanoic acid | 787 |
| 22.03 | Oleic anhydride | 639 |
| 23.02 | 9-octadecenamide | 798 |
| 23.30 | Octadecanamide | 605 |

FIG. 21 – Table 6

| Elemental analysis of bio-oil fraction collected at 420 °C from *Chlorella sp.** ||
|---------|--------|
| Element | Wt%    |
| C       | 74.56  |
| H       | 11.11  |
| N       | 1.87   |
| O       | 12.46  |
| *HHV ~ 41 MJ/Kg ||

FIG. 24 – Table 7

THERMAL FRACTIONATION OF BIOMASS OF NON-LIGNOCELLULOSIC ORIGIN FOR MULTIPLE HIGH-QUALITY BIOFUELS

CROSS-REFERENCE TO RELATED APPLICATIONS

This is a continuation-in-part application of U.S. patent application Ser. No. 13/294,510, filed under 35 U.S.C. §111(a) on Nov. 11, 2011, now U.S. Pat. No. 8,927,240, issued Jan. 6, 2015; which claims the benefit of U.S. Provisional Application Ser. No. 61/413,177, filed under 35 U.S.C. §111(b) on Nov. 12, 2010. The entire disclosures of all the aforementioned applications are expressly incorporated herein by reference for all purposes.

STATEMENT REGARDING FEDERALLY SPONSORED RESEARCH

This invention was made with government support under Grant Number CHE-1230609, awarded by the National Science Foundation, and Grant Number DE-EE0005993, awarded by the Department of Energy. The government has certain rights in this invention.

TECHNICAL FIELD AND INDUSTRIAL APPLICABILITY OF THE INVENTION

The present invention relates to a method for production of multiple biofuels through thermal fractionation of non-lignocellulosic biomass feedstocks.

BACKGROUND

There is a growing interest towards development of renewable fuels as a result of increasing global energy consumption, finite petroleum resources, and global warming concerns. Non-food biomass materials, such as microalgae, can be viable feedstocks for environmentally sustainable biofuels. In general, microalgae have greater areal productivity than terrestrial plants, can be grown on non-agricultural and marginal lands, and can use low quality water and nutrients from waste streams. Several strains of microalgae are known to accumulate triglycerides—a platform chemical that is in current use for the production of biodiesel as well as high value oleochemicals. However, a key bottleneck in the commercial development of algal bio-refineries is a lack of scalable and viable conversion processes that can produce fuels as well as value-added chemicals.

One approach to downstream processing involves extraction of triglycerides from algal cells using organic solvents such as chloroform and hexane. However, due to the microscopic cell size and robust cell walls, this approach requires additional mechanical disruption. After extraction, the solvent must be separated, usually through evaporation, to recover the triglycerides. The recovered triglycerides may then be further converted to hydrocarbon fuels via thermo-catalytic de-carboxylation or hydro-cracking. Alternately, if biodiesel is the desired product, fatty acid methyl esters (FAMEs) may be more easily obtained from cellular triglycerides through in situ transesterification where oleaginous biomass is directly reacted with a mixture of methanol and catalyst without prior solvent extraction. However, FAME recovery from the reaction mixture still requires solvent extraction (e.g. with chloroform or hexane) followed by solvent evaporation. Solvent extraction methods have, so far, proven effective only with dry biomass, and in situ transesterification is likely more sensitive to even small amounts of moisture in the biomass. In methods involving solvent use, the post-extraction solid residues, generally rich in protein, may also need extensive treatment for solvent removal before use as animal feed or fertilizer.

As an alternative to solvent extraction, thermochemical conversion processes such as pyrolysis and hydrothermal liquefaction can be employed to obtain bio-oil or bio-crude for subsequent conversion to liquid fuels and value-added chemicals. Thermo-chemical methods are generally less species-sensitive than solvent extraction. In addition, these processes can produce fuel/chemical precursors from even the non-triglyceride portions of algal cells (e.g. carbohydrates, other lipids, and proteins). However, thermo-chemical processes, as traditionally applied, produce bio-oils/bio-crude that contains a complex and highly heterogeneous mixture of chemical compounds—long chain fatty acids from degradation of triglycerides and other cellular lipids, short chain oxygenates (e.g. aldehydes, ketones, organic acids, water, and alcohols) from degradation of carbohydrates and N-compounds from protein degradation. Oxygenates in bio-oil lower its heating value and degrade/polymerize over time to produce humins or char. In addition, algal bio-oil/bio-crude obtained from traditional thermo-chemical processes would consist of a broad molecular weight distribution of chemical species—longer chain products from triglyceride degradation and lower molecular weight compounds from degradation of carbohydrate and protein—that would necessitate further distillation into suitable fuel fractions and result in additional energy inputs for fuel production.

SUMMARY OF THE INVENTION

Provided herein is a two-step method of thermal fractionation. The two-step method is a method of pyrolytic thermal fractionation of microalgae biomass containing a protein component and a triglyceride component, with or without an additional carbohydrate component. The method includes the steps of: (a) heating the microalgae biomass to a first volatilization temperature of a first component comprising at least one of proteins or carbohydrates, and holding the first volatilization temperature of the heated microalgae biomass constant for a first period of time until substantially no further mass loss of the first component occurs, thereby producing a first volatilized vapor product derived from proteins and/or carbohydrates, wherein the first volatilization temperature is in the range of from about 180° C. to about 360° C.; (b) removing, from the biomass remaining in step (a), and recovering, the first volatilized vapor product derived from thermal treatment of the microalgae biomass in step (a); (c) heating the microalgae biomass remaining from step (b) to a second volatilization temperature of a second component comprising triglycerides, and holding the second volatilization temperature of the heated microalgae biomass constant for a second period of time until substantially no further mass loss of the second component occurs, thereby producing a second volatilized vapor product derived from the triglycerides, wherein the second volatilization temperature is in the range of from about 370° C. to about 500° C.; and (d) removing, from the microalgae biomass remaining from step (c), and recovering, the second volatilized vapor product derived from thermal treatment of the microalgae biomass in step (c).

In certain embodiments, step (a) comprises simultaneously volatilizing proteins and carbohydrates. In certain embodiments, the second volatilized vapor product comprises one or more of triglycerides, long-chain fatty acids, di-glyceride, mono-glyceride, or hydrocarbons. In certain embodiments, the first volatilized vapor product comprises one or more of organic acids, furans, N-compounds, water, aldehydes, ketones, or phenols.

In certain embodiments, the first volatilization temperature ranges from about 240° C. to about 340° C. In certain embodiments, the first volatilization temperature ranges from about 310° C. to about 330° C. In certain embodiments, the first volatilization temperature is about 320° C. In certain embodiments, the second volatilization temperature ranges from about 390° C. to about 450° C. In certain embodiments, the second volatilization temperature ranges from about 410° C. to about 430° C. In certain embodiments, the second volatilization temperature is about 420° C.

In certain embodiments, the microalgae biomass comprises *Chlorella* sp. In certain embodiments, the microalgae biomass comprises *Scenedesmus* sp.

In certain embodiments, the first period of time is in the range of from about 5 minutes to about 30 minutes. In certain embodiments, the second period of time is in the range of from about 5 minutes to about 30 minutes. In certain embodiments, the first period of time is in the range of from about 10 minutes to about 15 minutes. In certain embodiments, the second period of time is in the range of from about 10 minutes to about 15 minutes. One or both of the first and second periods of time can be lengthened for a time sufficient to increase production of the respective volatized compounds.

In certain embodiments, the method further comprises combusting the first volatilized vapor product for recovery of process heat. In certain embodiments, the method further comprises passing the first volatilized vapor product through hydro-denitrification and hydro-deoxygenation processes to reduce nitrogen and oxygen content of products. In certain embodiments, the method further comprises subjecting the first volatilized vapor product to a downstream purification step to recover nitrogen- and/or oxygen-containing compounds. In certain embodiments, the method further comprises esterifying the second volatilized vapor product to produce fatty acid alkyl esters or biodiesel. In particular embodiments, the esterification comprises gas-phase reactions with one or more alcohol vapors. In particular embodiments, the esterification is conducted with a solid or mineral acid catalyst. In particular embodiments, the esterification is conducted without a catalyst. Further provided is the product of the esterification.

Further provided is the product of the two-step method described herein.

Other systems, methods, features, and advantages of the present disclosure will be or will become apparent to one with skill in the art upon examination of the following drawings and detailed description. It is intended that all such additional systems, methods, features, and advantages be included within this description, be within the scope of the present invention, and be protected by the accompanying claims. Overall, methods for the production of multiple biofuels through thermal fractionation of non-lignocellulosic biomass are described.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the Patent Office upon request and payment of the necessary fee.

(FIG. 1A) and *Scenedesmus* sp. (FIG. 1B).

(FIG. 3A) and *Scenedesmus* sp. (FIG. 3B). Yellow residual weight (dashed) and derivative weight loss curves (solid lines) show pyrolysis of the protein and carbohydrate fractions of the biomass (T<320° C.). Green curves show thermograms of the samples obtained after removal of pyrolyzable protein and carbohydrate, which indicate that prolonged exposure to lower temperatures does not negatively impact the thermal decomposition characteristics of the constituent triglycerides. The arrows indicate the temperature path followed.

(FIG. 4A) and *Scenedesmus* sp. (FIG. 4B). The non-isothermal zone (Region I) shows weight loss during temperature ramp from 250° C. to 320° C. Region II shows weight loss during isothermal heating at 320° C.

(FIG. 6A) and *Scenedesmus* sp. (FIG. 6B) in a micro-pyrolyzer experiment. The chemical compounds were identified using the NIST2008 library. Refer to FIGS. 7-8 for full list of chemical compounds identified in this chromatogram.

FIG. 7: Table 1, showing confidence value of chemical compounds present in protein as well as carbohydrate-based bio-oils of *Chlorella* sp. Confidence limits range from 0 to 1000, and numbers higher than 600 indicate the presence of the particular compound with high certainty (as per NIST 2008 library).

FIG. 8: Table 2, showing confidence value of chemical compounds present in protein as well as carbohydrate-based bio-oils of *Scenedesmus* sp. Confidence limits range from 0 to 1000, and numbers higher than 600 indicate the presence of the particular compound with high certainty (as per NIST 2008 library).

(FIG. 13A) and *Scenedesmus* sp. (FIG. 13B) following Step 1 heating at 320° C. in micro-pyrolyzer experiments.

FIG. 14: Table 3, showing confidence value of chemical compounds present in bio-oils formed during isothermal heating at 420° C. of *Chlorella* sp. in micro-pyrolyzer experiments.

FIG. 15: Table 4, showing confidence value of chemical compounds present in bio-oils formed during isothermal heating at 420° C. of *Scenedesmus* sp. in micropyrolyzer experiments.

FIG. 17: GC-MS chromatogram of bio-oil collected from Step 1 of fixed-bed pyrolytic fractionation performed on oleaginous *Chlorella* sp. at 320° C. 2.6 mg bio-oil was dissolved in 1 mL of methanol for analyses.

FIG. 18: Table 5, showing confidence values of chemical compounds present in bio-oil collected during Step 1 (320° C.) of bench-scale fixed-bed experiments with oleaginous *Chlorella* sp. at 320° C.

FIG. 21: Table 6, showing confidence values of chemical compounds present in bio-oil collected during Step 2 of bench-scale fixed-bed experiments with oleaginous *Chlorella* sp. at 420° C.

FIG. 24: Table 7, showing an elemental analysis of bio-oil collected during Step 2 of bench-scale fixed-bed pyrolytic fractionation experiments with *Chlorella* sp. at 420° C.

DETAILED DESCRIPTION OF THE INVENTION

Figure 1A:
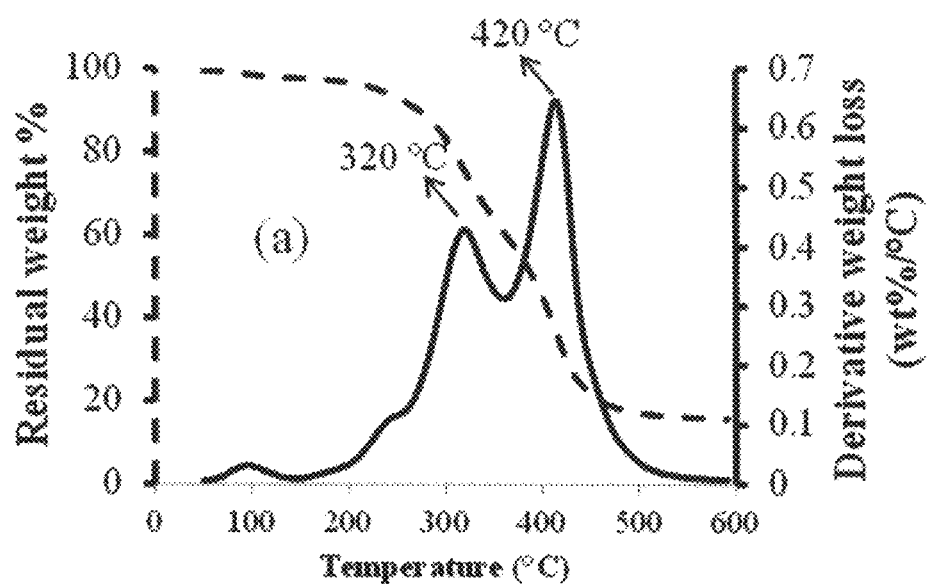
FIGS. 1A-1B: Graphs show the residual weight (dashed) and derivative weight loss (solid lines) curves obtained during thermal degradation of *Chlorella* sp.

Throughout this disclosure, various publications, patents, and published patent specifications are referenced by an identifying citation. The disclosures of these publications, patents and published patent specifications are hereby incorporated by reference into the present disclosure to more fully describe the state of the art to which this invention pertains.

Provided herein are various "pyrolytic fractionation" approaches whereby products from pyrolysis of triglycerides—the highest energy component of oleaginous microalgae—are obtained as more homogenous bio-oils. The validity of pyrolytic fractionation is demonstrated with oleaginous feedstocks such as *Chlorella* sp. and *Scenedesmus* sp. These processes have decreased energy costs and can be utilized in an integrated design for the production of drop-in fuels and oleochemicals through pyroytic fractionation. The methods involve heating the biomass feedstock in an inert and oxygen-free environment, and are performed at lower temperatures than conventional pyrolysis. The methods result in the production of bio-oils, gases, and char. Integration of hydrotreatment processes with pyrolysis can make the entire process more energy efficient through heat integration (condensation and re-vaporization of bio-oils is avoided) and reduce storage/handling/transport costs as well as associated loss of bio-oil quality.

In one particular aspect, provided is a method that enables the recovery of bio-oil from lipids following just two pyrolysis steps. The method involves heating a biomass to a first temperature at which proteins and carbohydrates volatilize, recovering and removing the volatilized compounds (also referred to as volatilized vapor products), then heating the biomass to a second temperature at which lipids such as triglycerides volatilize, and removing and recovering the volatilized compounds. In accordance with the present disclosure, proteins and carbohydrates can be volatilized in a single pyrolysis step at a temperature in the range of from about 180° C. to about 360° C. Following removal of the volatilized compounds produced from the proteins and carbohydrates, the triglycerides can be volatilized at a temperature in the range of from about 370° C. to about 500° C. The volatilized compounds can be condensed to produce one or more bio-oils. Non-condensable compounds can be recovered as syngas, which can be used as fuel, for combustion, or for power generation. The two-step process is capable of producing high calorific triglyceride-specific bio-oil from oleaginous algal biomass. In certain embodiments of the two-step process, the products have little, if any, contamination of N-compounds and oxygenates from carbohydrate degradation.

Biomass of non-lignocellulosic origin is typically composed of one or more of three factional components—(1) proteins or protein-derived materials; (2) carbohydrates such as starches, starch-like polymers, cellulosic polymers, or hemicellulosic polymers; and (3) lipids, or oils (such as triacylglycerides or other lipids). In alternative methods described herein, the three biopolymer fractions can be separated in a three-step process instead of a two-step process. Thus, non-ligninaceous biomass feedstock can be thermally fractionated using distinct, non-overlapping degradation temperature windows of the component biopolymers found in the biomass.

One of the concerns with thermochemical processing of protein-containing biomass is contamination of bio-oil with nitrogen-containing compounds (such as pyrozole, pyridine, maltol etc.) derived from protein. N-containing fuels are of low quality and may not pass fuel standards due to formation of $NO_x$ upon combustion. In addition, when bio-oils are upgraded through catalytic hydrogenation and deoxygenation, the presence of N-compounds can poison the catalysts.

Storage lipids in microalgae volatilize, or thermally degrade, at distinctly higher temperatures than proteins and carbohydrates. Thus, oil and gas can be recovered individually from each of these fractions, if desired. However, in accordance with the present disclosure, the proteins and carbohydrates can be volatilized together in a single step, which enables the recovery of bio-oil from the lipid fraction without needing to undertake a third heating step.

During practice of the thermal fractionation processes described herein, the relatively low value fuel obtained from protein and carbohydrate degradation can be used on-site to generate process heat. Alternatively, the pyrozole- and pyridine-like compounds from protein degradation, as well as the pyranoses, organic acids, aldehydes, and ketones from carbohydrate degradation, can be isolated from this bio-oil fraction as high value products or precursors for N-based chemicals and polymers. It is also possible to convert bio-oil from the protein and carbohydrate fraction into commercial fuel after N- and O-removal, such as by hydro-denitrification and hydro-deoxygenation. A mixture of volatilized vapor products from the protein and carbohydrate fraction can be passed through hydro-denitrification and hydro-deoxygenation processes for integrated and on-stream removal of N and O. A mixture of volatilized vapor products resulting from the protein and carbohydrate materials can also be subjected to downstream purification to recover high value oxygenates or N-compounds. Alternatively, the volatilized compounds produced from the protein and carbohydrate materials can be substantially combusted for recovery of process heat.

The volatilized compounds produced from the proteins and carbohydrates can be mixed with $H_2$. This mixture can then be passed through a catalytic reactor to cause one or more of hydrogenation and deoxygenation of the volatilized compounds to occur. The hydrogenated and/or deoxygenated volatilized compounds can then be condensed to form substantially vehicle-ready fuel.

The biomass remaining after thermal removal of protein and carbohydrates can be further processed to recover bio-oils from lipids, as a separate fraction. The lipid-derived oils may need minor or no further processing. Lipids are mostly hydrocarbons with low oxygen and therefore the pyrolysis products from this fraction do not need extensive hydrogenation or deoxygenation. However, hydrotreatment or hydro-decarboxylation can be used to convert fatty acids in the lipid-derived biooils into hydrocarbons. According to the methods described herein, only a fraction of the total bio-oil produced from the feedstock requires extensive upgradation. The volatilized compounds produced from the lipids can be esterified to produce fatty acid alkyl esters and/or biodiesel. The esterification can be conducted using gas-phase reactions with one or more alcohols. The esterification can occur with the assistance of solid or liquid acid catalysts. The esterification can also occur without the assistance of solid or liquid acid catalysts.

The steps of recovering and removing volatilized compounds can be aided with the use of a purge gas, such as hydrogen or nitrogen. Purging one or more steps with the purge gas can allow the maintenance of anoxic conditions. The gas can substantially continuously remove one or more volatilized compounds being generated. The purge gas can be inert, but does not need to be inert. When hydrogen is used as a purge gas, it can result in simultaneous and at least partial hydrogenation of the volatilized compounds. The flow rate of the purge gas can be substantially maintained such that residence times of the volatilized compounds resulting from the biomass feedstock are about 2 seconds or less. The flow rate of the purge gas can also be substantially maintained for a vapor residence time sufficient to minimize degradation of volatilized compounds into non-condensable gases, such as CO, $CO_2$, $CH_4$, or $H_2$.

The residue biomass remaining after the recovery of all volatilized compounds can be recovered as biochar. The char recovered at the end of the thermal fractionation processes has a composition and properties similar to char resulting from traditional pyrolysis. The char can be utilized as a soil amendment, as fertilizer, or as a charcoal replacement. The biochar can also be combusted on site for generation of process heat.

The present disclosure provides evidence of the thermal fractionation of non-ligninaceous biomass using certain algae species (such as *Scenedesmus* sp. and *Chlorella* sp.) or soybean flour. Though particular microalgae species are utilized in the examples described herein, it is to be understood that the presently described methods can be practiced using a wide variety of non-ligninaceous biomass. Suitable non-ligninaceous biomass includes those having volatilizible combinations of one or more of: carbohydrates and proteins; carbohydrates and lipids; proteins and lipids; and proteins, carbohydrates, and lipids. By way of non-limiting examples, suitable non-ligninaceous biomass includes algae, microalgae, macroalgae, bacteria such as cyanobacteria, fungi, yeast, plants and plant parts, stalks, and seeds. In certain examples, the biomass is soybean, corn, canola, jatropha, or camelina. In certain other examples, the biomass is a microalgae species such as *Scenedesmus* sp. or *Chlorella* sp. The biomass may be present as an at least partially wet feedstock, or as a substantially dry feedstock.

In certain non-limiting examples, the present disclosure identifies the temperature windows of degradation of each of these polymers through thermogravimetric analyses (TGA) where temperatures were continuously increased over time at a constant rate. Complete volatilization of each of these fractions in both biomass types was then verified by heating samples up to the degradation temperatures followed by an isothermal heating.

The appropriate temperatures of heating for one or more of the pyrolysis steps described herein can be determined through thermogravimetric analysis (TGA). In TGA, samples of known weight are continuously heated at a programmed rate and the sample weight loss is monitored over time. Simultaneously, the rate of mass loss is also recorded. When the weight loss occurs rapidly (for example, at the volatilization temperature of a component) the "rate of weight loss profile" shows a peak. This peak helps identify the volatilization window for the component. Thus, determining the appropriate temperatures includes: first, heating the biomass in a TGA instrument to determine temperature zones of most rapid mass loss by volatilization, i.e., derivative mass loss "peaks"; and second, verifying thermal fractionation by heating samples sequentially to each of the temperatures where these peaks occur, followed by an isothermal hold step until the stoppage of weight loss at each peak.

EXAMPLES

The present disclosure is further defined in the following Examples, in which all parts and percentages are by weight and degrees are Celsius, unless otherwise stated. It should be understood that these Examples, while indicating certain non-limiting embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference. The following examples are intended to illustrate certain preferred embodiments of the invention and should not be interpreted to limit the scope of the invention as defined in the claims, unless so specified. The value of the present disclosure can thus be seen by reference to the Examples herein.

Example 1: Pyrolytic Fractionation Simulation

*Chlorella* sp. (a natural isolate) and *Scenedesmus* sp. were heterotrophically grown on glucose using previously described culture conditions (Chowdhury & Viamajala, 2011; Nelson, 2010, incorporated herein by reference). Stationary phase cultures that were rich in triglycerides were centrifuged (2500×g), washed with de-ionized water, and freeze-dried (Labconco Freezone 2.5 L bench-top freeze drying system, Kansas city, MO) to obtain feedstocks. Soy oil was purchased from Spectrum Naturals (Boulder, Colo.) and used as received. GC-grade 1,3-diolein was purchased from Sigma-Aldrich (St. Louis, Mo.).

10-15 mg of freeze dried algae was added to 1 mL of chloroform in a 2 mL stainless steel bead beating vials with polypropylene plug cap (BioSpec Products, Bartlesville, Okla.). A Mini-Beadbeater-1 (BioSpec Products, Bartlesville, Okla.) was used to agitate the stainless steel vials. Each vial was agitated for 20 s at 2500 oscillations per minute and then cooled in an ice bath for 1 min. Total bead beating time was 45 min. The organic phase in stainless steel vials was transferred to 5 mL glass vial. Stainless steel vials were then rinsed with 1 mL of chloroform and added to the organic phase collected. This organic phase was filtered and transferred to GC vials for quantification of triglycerides, monoglycerides, di-glycerides, and fatty acids using gas chromatography equipped with flame ionization detector (GC-FID).

TG and DSC analyses were performed on a TA Instruments SDT Q600 series analyzer (Schaumburg, Ill.) that provides simultaneous measurement of weight change and differential heat flow on a single sample. For these measurements, 10-15 mg of biomass was loaded into one alumina crucible while a second identical crucible served as a reference. $N_2$ was used as the carrier gas and also to maintain inert atmosphere. The flow rate of $N_2$ was kept at 100 mL Overall thermal degradation behavior of biomass feedstocks was determined by heating the samples from room temperature to 600° C. at a constant ramp rate of 20° C. min' under $N_2$ atmosphere.

A two-stage heating protocol was used where samples were successively heated to 320° C. and 420° C. and maintained isothermal for 10 min at each of these temperatures. The 10 min isothermal incubation time at each stage was chosen since little, if any, weight loss was detected after this period. The inter-stage heating rate was 20° C. min'.

Pyrolysis experiments were performed on a CDS Pyroprobe™ 5200 unit (CDS Analytical, Oxford, Pa.) connected to a Bruker 450 gas chromatograph (GC) equipped with a 300 series mass spectrometer (MS) (Billerica, Mass.). An open-ended quartz tube (1" long) served as a micro-pyrolysis reactor in the Pyroprobe™ system. The reactor temperature was set and maintained using a resistively heated platinum element coiled around the tube. Vapors from pyrolysis were routed through a gas trap packed with Tenax® adsorbent material. After pyrolysis, the volatiles from the trap were desorbed and sent to the GC-MS for analysis. A heated transfer line connected the trap to the GC injector.

Before the start of the experiment, approximately 1 mg of biomass sample was placed into the quartz tube for pyrolysis. During the experiment, the system environment (including reactor and trap) was kept inert by applying a continuous helium purge (50 mL min'). To simulate pyrolytic fractionation, a three stage heating protocol was used similar to the TG-DSC experiments described above. At each stage, the pyrolysis reactor was heated to the desired set point (320° C. and 420° C.) and maintained isothermal for 15 min. Similar to the TG-DSC experiments, the inter-stage heating rate was kept at 20° C. min'. The vapors generated during pyrolysis were adsorbed in the gas trap that was held at a much lower temperature of 50° C. to facilitate better retention of the volatiles. Following the completion of each pyrolysis stage, the reactor was allowed to cool down to room temperature while the trap was heated for 7 min to desorb the volatiles for GC analysis. Helium was used as the purge gas (100 mL min'). For the first two desorption stages, the trap temperature matched the pyrolysis temperature. However, the trap was heated only up to 350° C. in the third desorption stage since Tenax® degrades above this temperature. Desorbed volatiles were routed to the GC injector via a transfer line that was also maintained at the same temperature as the trap.

GC-MS analysis was synchronized with the desorption steps. An Agilent DB-5MS fused silica capillary column (30 m×0.25 mm×0.25 µm film thickness, Agilent Technologies, Santa Clara, Calif.) was used in the GC. The injector temperature was 300° C. and a split ratio of 1:100 was maintained. Helium, used to purge the trap, also served as the carrier gas (1.0 mL min$^{-1}$) in the GC column. The temperature program of the GC column was as follows: constant temperature of 50° C. for 7 min (to match the time for desorption of volatiles from the trap) followed by temperature ramp to 300° C. at 10° C. min$^{-1}$, and finally a constant temperature of 300° C. for 3 min. The MS source was maintained at 150° C. The transfer line (between GC and MS) remained at 300° C. Chemical compounds corresponding to chromatogram peaks were identified using the NIST2008 mass spectral database. Only compounds with a "confidence" value above 600 were reported.

Pyrolytic fractionation experiments were conducted in a quartz tubular reactor (L=43 cm, OD=2.54 cm) placed in a horizontal split shell electric furnace (Applied Test Systems Inc., Butler, Pa.). A K-type thermocouple remained in contact with the biomass during the experiments to directly measure the temperature inside the pyrolysis chamber. The outlet of the reactor was connected to a glass condenser that had a continuous flow of ethylene glycol (−15° C.) as a coolant. $N_2$ was continuously passed through the reactor during pyrolysis to maintain oxygen-free conditions. The flow rate of $N_2$ was maintained at 1 L/min using mass flow controllers (model 316L MCS, Alicat Scientific, Tucson, Ariz.). The reactor and glass condenser were connected by ¼" stainless steel tubing that was maintained at pyrolysis temperature using heating tape to prevent in-line condensation. ⅛" stainless steel tubing was used for all other connecting lines. Lines carrying $N_2$ were first routed through the pyrolysis furnace to preheat the gases before entering the reactor.

Before the start of each experiment, 5 g of biomass was placed in the tubular reactor using quartz wool as a support, and the reactor was purged with $N_2$ (1 L/min) for 15 min to remove air from the system. Thereafter, the pyrolysis furnace was heated to the set-point temperature (i.e., 320° C. and 420° C.) at a ramp rate of 30° C./min (verified through monitoring the thermocouple readout). It was observed that all biomass samples in the pyrolysis reactor reached reaction temperatures within 20 min. After reaching set-point, the reactor was maintained at that temperature for 10 min. The pyroprobe experiments showed that this duration was sufficient for the pyrolysis reactions to be complete. Based on the dimensions of the pyrolysis reactor and gas flow rates used ($N_2$), the vapor residence time (reactor to condenser) was calculated to be <4 s.

At the end of the experiment, the pyrolysis reactor was cooled to room temperature and bio-oils (collected in the condenser) were weighed (to calculate corresponding product yields) and stored at −20° C. for subsequent analyses as described below. The gas yields were determined by subtracting the mass of bio-oil and bio-char collected from the initial mass of feedstock added to the reactor.

During these experiments, the liquid products obtained as well as solids residues obtained after pyrolysis at 320° C. were collected to perform further GC, GC/MS, CHN, and FAME analysis. Solids residues obtained at 320° C. were then pyrolyzed again at 420° C. to produce char and triglyceride-based bio-oil.

Figure 1B:
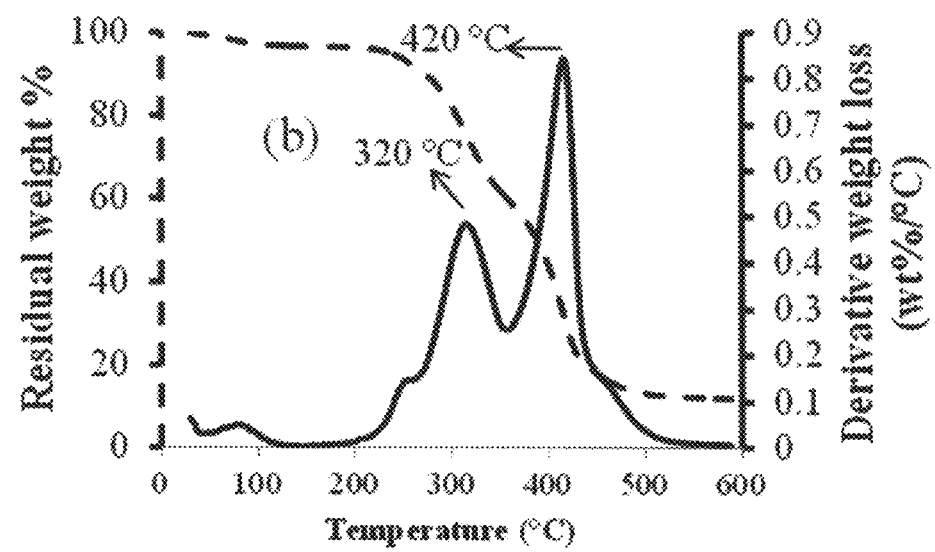

FIGS. 1A-1B show the residual weight (dashed) and derivative weight loss (solid lines) curves obtained during thermal degradation of *Chlorella* sp. (FIG. 1A) and *Scenedesmus* sp. (FIG. 1B). FIGS. 1A-1B show two well-separated derivative weight loss peaks at 320° C. and 420° C. for both of these oleaginous algal samples. Based on other examples described below, the derivative weight loss peak at 320° C. resulted from degradation of algal proteins and carbohydrates, while the derivative weight loss peak at 420° C. is attributed to volatilization of the triglyceride fraction of algal samples. TG analysis of soy oil (FIG. 2) confirmed that the peak at 420° C. was associated with pyrolysis of triglycerides.

Since the protein and carbohydrate fractions degrade at lower temperatures (280-350° C.) than triglycerides in oleaginous feedstocks (370-450° C.), a sequential exposure of biomass to these temperature intervals results in pyrolysis of proteins and carbohydrates followed by pyrolysis of triglycerides. Further, when condensed separately, this "pyrolytic fractionation" method produces triglyceride-specific bio-oils with low, if any, contamination by small molecular weight N- and O-compounds produced from carbohydrate and protein pyrolysis. One additional observation from these experiments is that triglyceride pyrolysis did not produce any measurable residues (FIG. 2), indicating that high product yields from triglycerides result from pyrolytic fractionation.

Figure 3A:
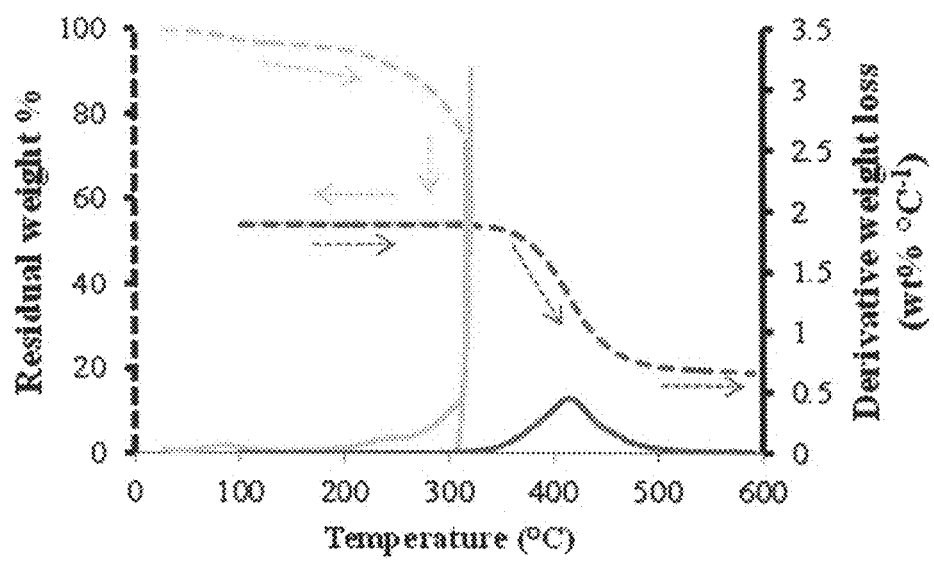
FIGS. 3A-3B: TG profiles resulting from pyrolytic fractionation of the protein as well as carbohydrate portion of *Chlorella* sp.
Figure 3B:
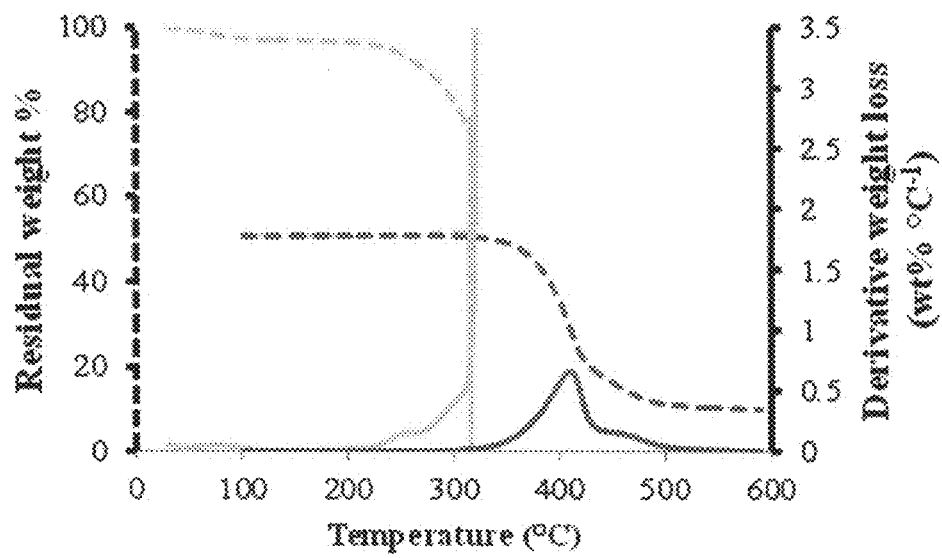

FIGS. 3A-3B show TG profiles resulting from pyrolytic fractionation of the protein as well as carbohydrate portion of (a) Chlorella sp. and (b) Scenedesmus sp. Yellow residual weight (dashed) and derivative weight loss curves (solid lines) show pyrolysis of the protein and carbohydrate fractions of the biomass (T<320° C.). Green curves show thermograms of the samples obtained after removal of pyrolyzable protein and carbohydrate, which indicate that prolonged exposure to lower temperatures does not negatively impact the thermal decomposition characteristics of the constituent triglycerides. The arrows indicate the temperature path followed for these experiments.

Figure 4A:
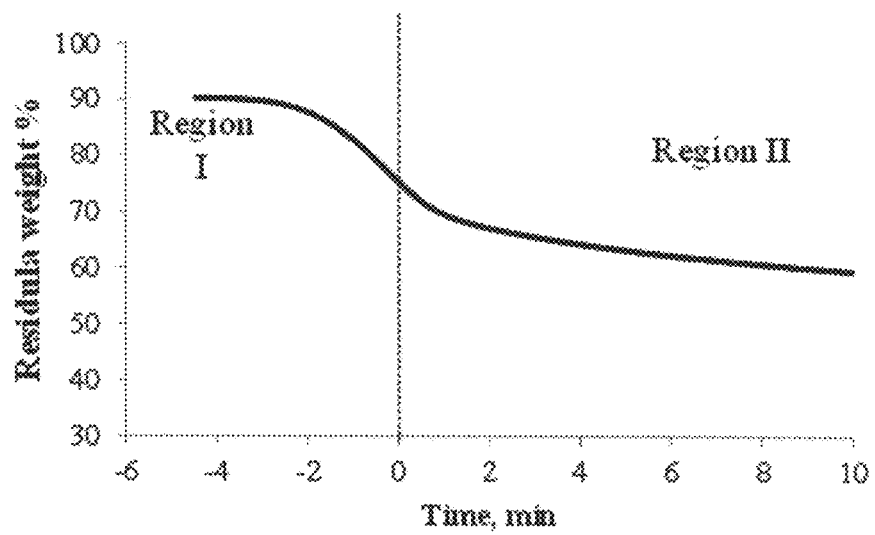
FIGS. 4A-4B: Kinetics of thermal degradation of the carbohydrate fractions of *Chlorella* sp.
Figure 4B:
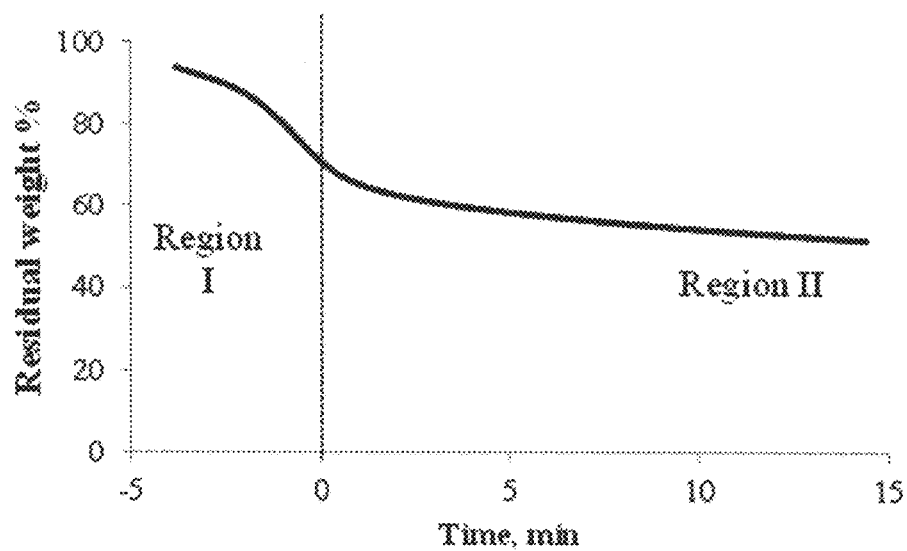

In this example, pyrolytic fractionation was simulated on the TG analyzer by step-wise heating. The dotted arrows in FIG. 3A indicate the temperature path implemented for pyrolysis. Samples were first heated to 320° C. and then incubated isothermally (yellow arrows) to pyrolyze the protein and carbohydrate fractions. After 10 min at this temperature, further weight loss was not significant (FIGS. 4A-4B), indicating that pyrolysis of the protein and carbohydrate fractions were substantially complete during this period. Thereafter, when the samples were cooled back to 100° C. and reheated (green arrows in FIG. 3A), the peak at 320° C. was absent from the thermogram (green differential weight loss profile in FIG. 3A), confirming the removal of thermally labile protein and carbohydrate fractions. Further heating resulted in triglycerides pyrolysis at 420° C., indicating that the removal of protein and carbohydrate did not have observable effects on the thermal characteristics of triglyceride fractions of Chlorella sp. (green derivative weight loss curves in FIG. 3A). Similar results were obtained with Scenedesmus sp. (FIG. 3B), when subjected to an identical thermal treatment for volatilization of protein and carbohydrate fractions. These observations indicate that prolonged exposure at 320° C. during pyrolytic fractionation did not result in triglyceride degradation or alter the thermal degradation characteristics of triglyceride fraction in the tested biomass samples. Overall, these results indicate that application of pyrolytic fractionation results in separate recovery of triglyceride-based bio-oils, with net product yields that are comparable with traditional pyrolysis. Further, the removal of water, organic acids, and nitrogenous and oxygenated compounds during pyrolysis at 320° C. results in low N- and O-content in triglyceride-based bio-oils.

Figure 5A:
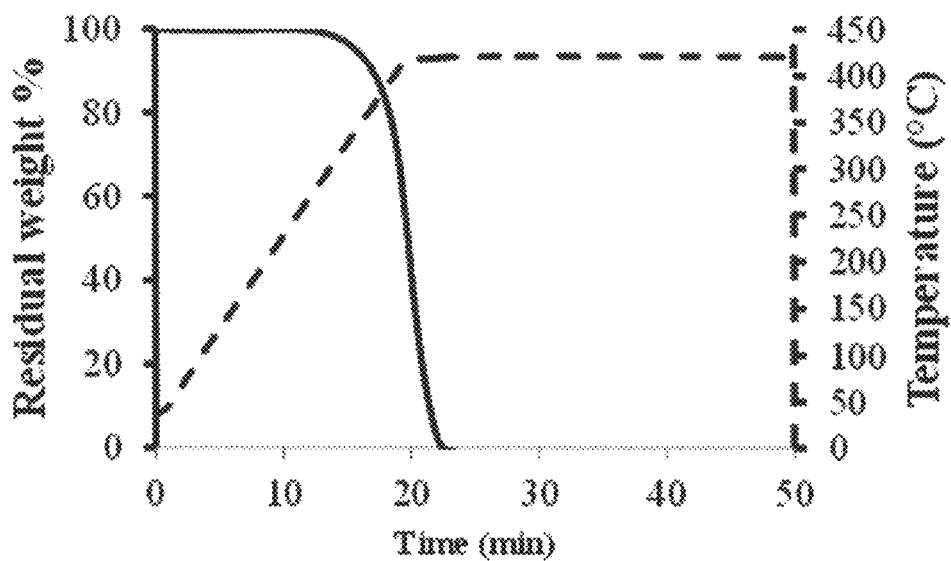
FIGS. 5A-5C: Kinetics of thermal degradation of the lipid fractions of tripalmitate (FIG. 5A), tristearate (FIG. 5B), and triolein (FIG. 5C). The non-isothermal zone shows weight loss during temperature ramp from room temperature to 420° C. The isothermal zone shows weight loss during incubation at 420° C.
Figure 5B:
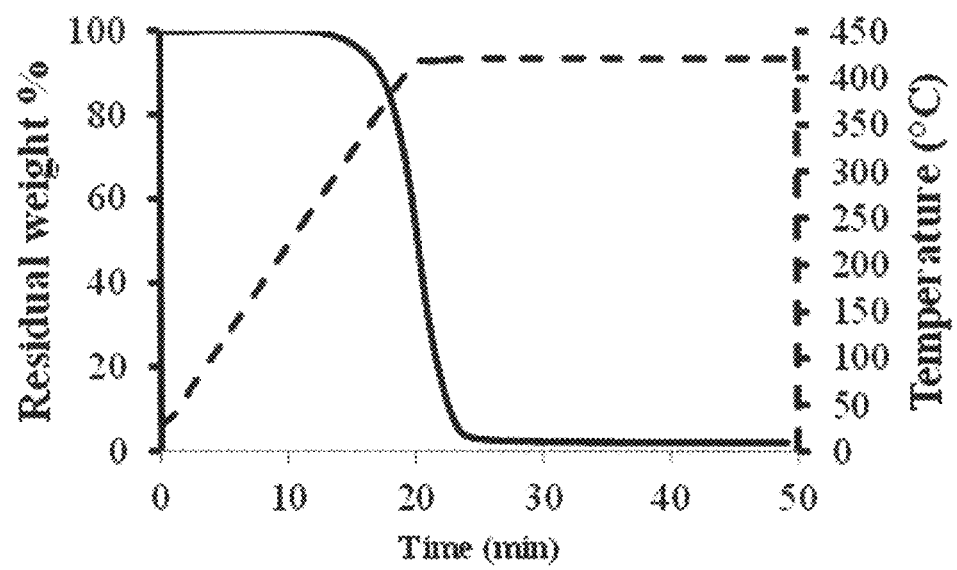
Figure 5C:
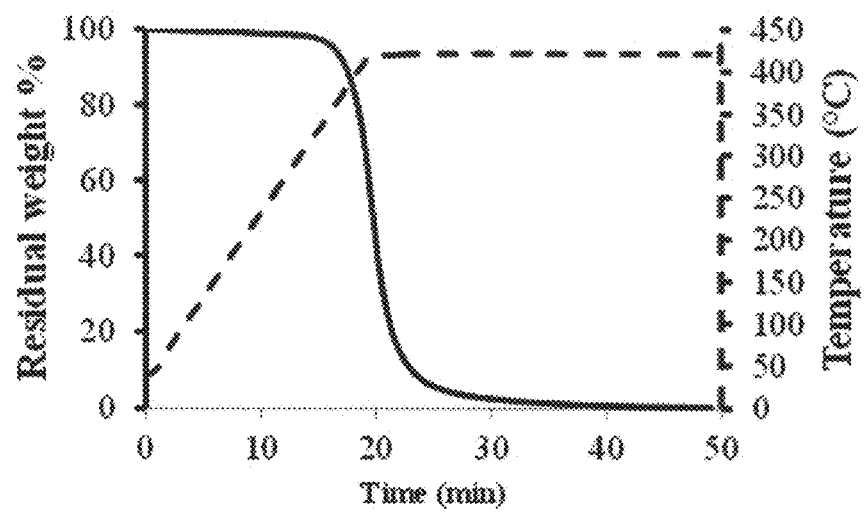

Finally, 10 min of isothermal incubation at 420° C. was sufficient to pyrolyze triglyceride fraction from biomass (FIGS. 5A-5C) that had been previously subjected to pyrolytic fractionation for thermal degradation of proteins and carbohydrates.

Example 2: Bench-Scale Micro-Pyrolysis

To assess the degradation products formed during pyrolytic fractionation of algal biomass within the temperature intervals predicted during TG studies, further experiments were performed on a Pyroprobe™ micro-pyrolysis system. Products obtained were analyzed using GC-MS and the product identities were used to verify the source biopolymer. While py-GC-MS (pyrolysis probe coupled with GC-MS) rapidly provides reliable information on the class of compounds produced, it is not a convenient tool for quantification. However, the py-GC-MS is commonly practiced as a screening method to determine optimal operating conditions for pyrolysis, and preliminary data obtained through py-GC-MS can be corroborated through larger-scale fixed/fluidized bed experiments.

Figure 6A:
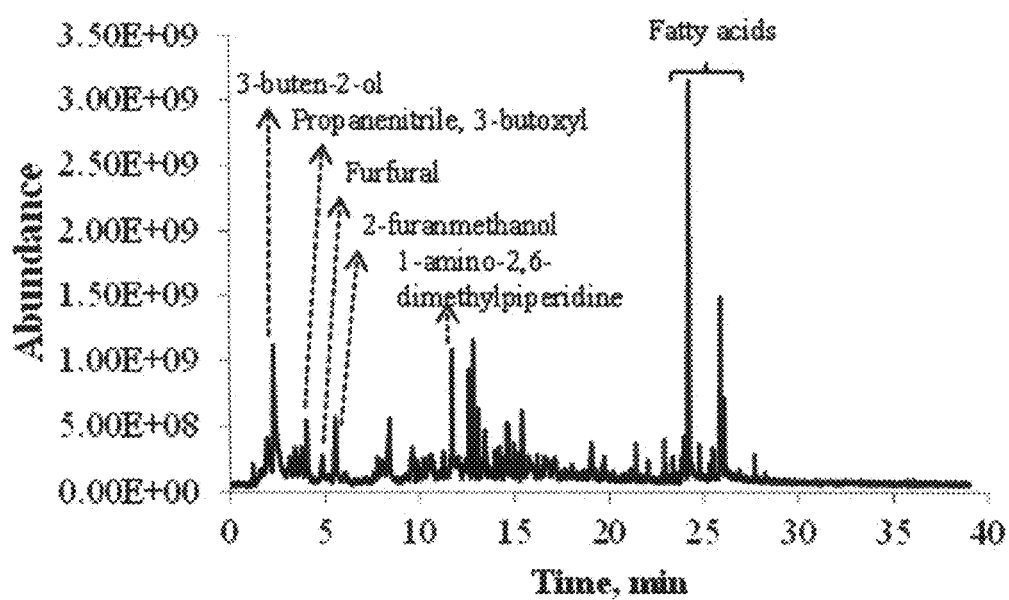
FIGS. 6A-6B: GC-MS chromatogram of protein as well as carbohydrate derived bio-oils from *Chlorella* sp.
Figure 6B:
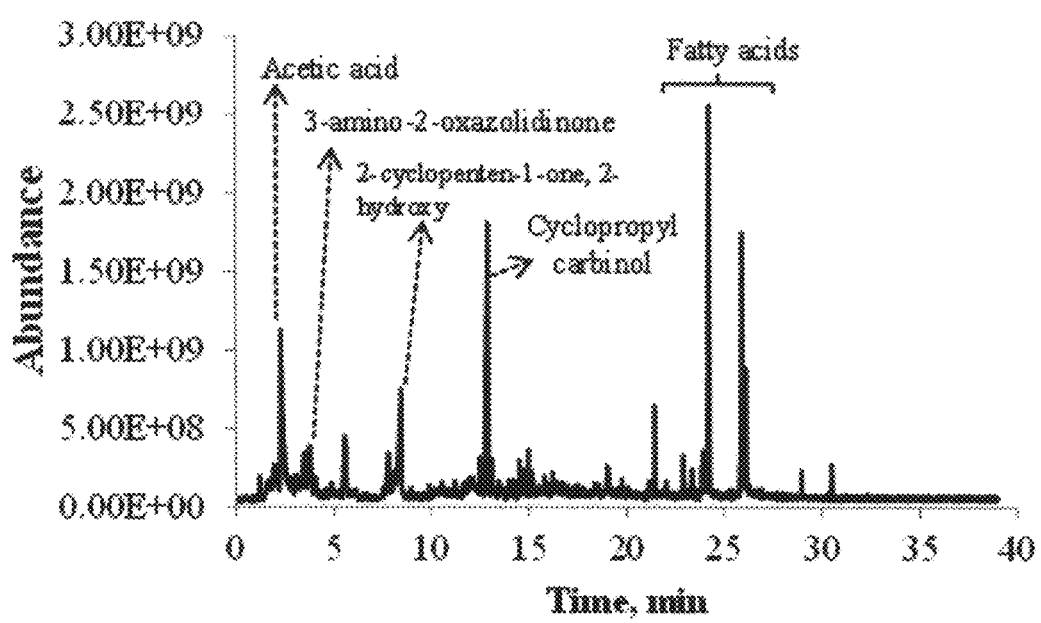

The first step of pyrolytic fractionation was implemented by heating and incubating the samples at 320° C. to degrade the protein and carbohydrate fractions of algal biomass. The GC chromatograms for the resulting products are shown in FIG. 6 (confidence levels of identified products are shown in Table 1 (FIG. 7) and Table 2 (FIG. 8)). At this temperature, pyrolysis products obtained from both Chlorella sp. and Scenedesmus sp. contained oxygenated compounds such as acetic acid, furfural, 2-furanmethanol, 2-(5H)-furanone, 2-hydroxy-2-cyclopenten-1-one, cyclopropyl carbinol, glucopyranose, levoglucosans, and maltols, which are typically formed from volatilization of carbohydrates. N-compounds were also present in pyrolysis products from both algae species. However, N-products were more diverse from Chlorella sp. pyrolysis (such as amino-2-oxazolidinone, 3-butoxy propanenitrile, 1-amino-2,6-dimethylpiperidine and indole) (FIG. 6A) than Scenedesmus sp. (only 3-amino-2-oxazolidinone was identified) (FIG. 6B). Without wishing to be bound by theory, it is believed this is due to the lower protein content of Scenedesmus sp. It is also possible that some N-compounds (e.g. $NH_3$ and $NO_x$) may not have adsorbed on the Tenax® trap of Pyroprobe™.

Figure 9A:
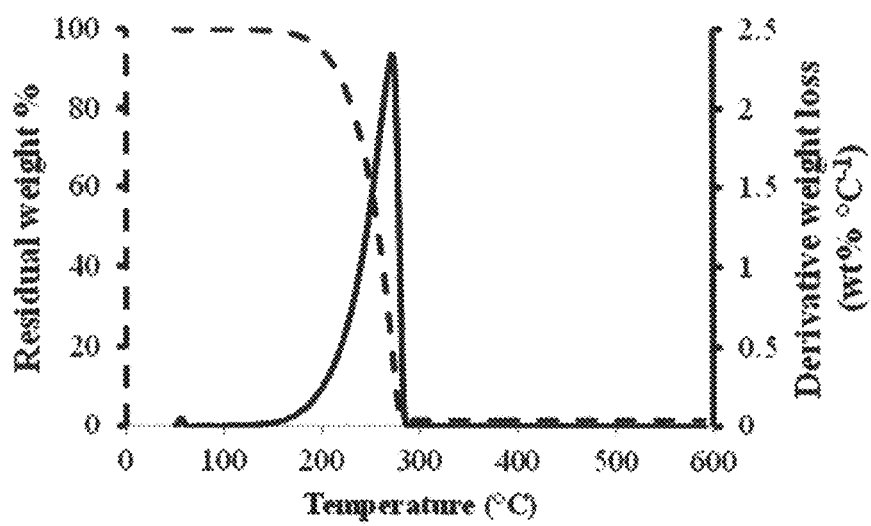
FIGS. 9A-9B: Derivative weight loss (solid) and residual weight (dashed) curves obtained during thermal degradation of myristic acid (C14) (FIG. 9A) and stearic acid (C18) (FIG. 9B).
Figure 9B:
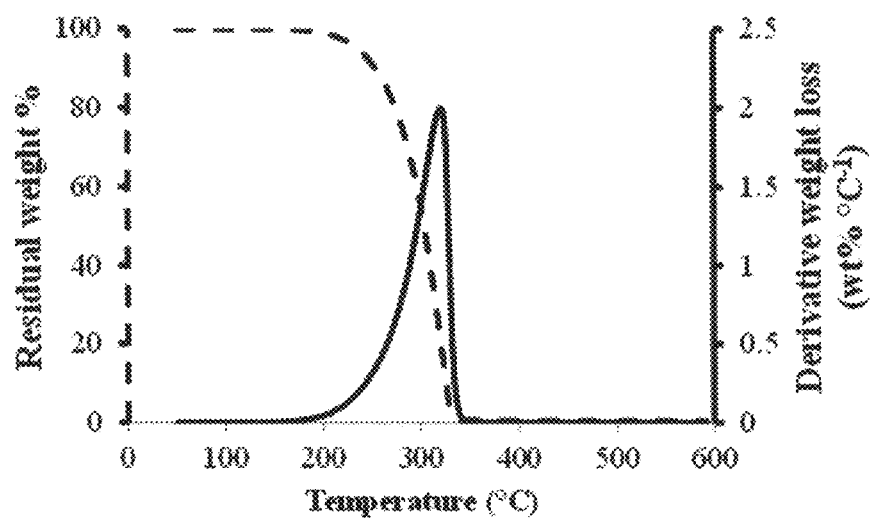
Figure 10:
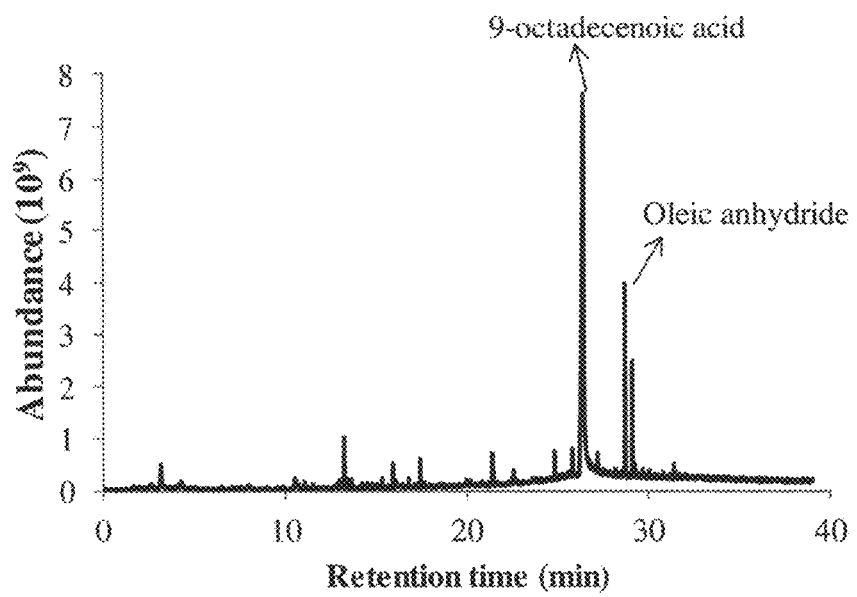
FIG. 10: GC-MS chromatogram of products from pyrolysis of 1,3-diolein at 320° C.
Figure 11:
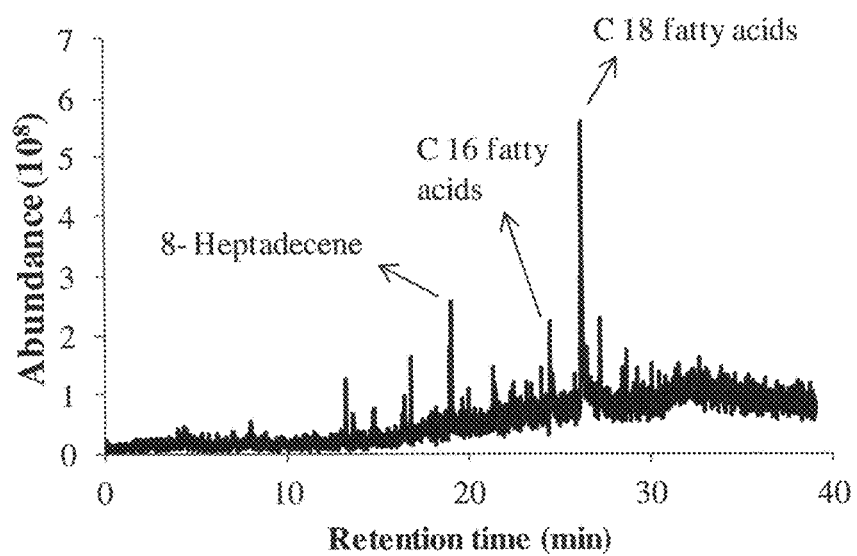
FIG. 11: GC-MS chromatogram of products from pyrolysis of soy oil at 320° C.

Relatively little is known about products of lipid pyrolysis. During the pyrolysis step at 320° C. intended for protein and carbohydrate pyrolysis, some C14-C18 hydrocarbons and fatty acids (e.g. octadecanoic acid) were also identified among the products. While cellular free fatty acids could have volatilized at this temperature (normal boiling points of C14-C18 fatty acids are in the range 250-300° C.; see FIGS. 9A-9B), limited breakdown of other lipids including glycerides or phospholipids may also have occurred. Indeed, when di- and tri-glycerides were pyrolyzed at 320° C., small amounts of fatty acids and fatty acid anhydrides were observed (FIGS. 10-11). Diglycerides underwent more thermal degradation than triglycerides, as is evident by the significantly higher concentrations of products obtained from diglyceride pyrolysis at 320° C. (note the order of magnitude difference in the y-axis scales between FIG. 10 and FIG. 11), indicating that smaller molecular weight lipids (possibly including monoglycerides and other short-chain lipids) are more thermally labile than triglycerides.

Figure 2:
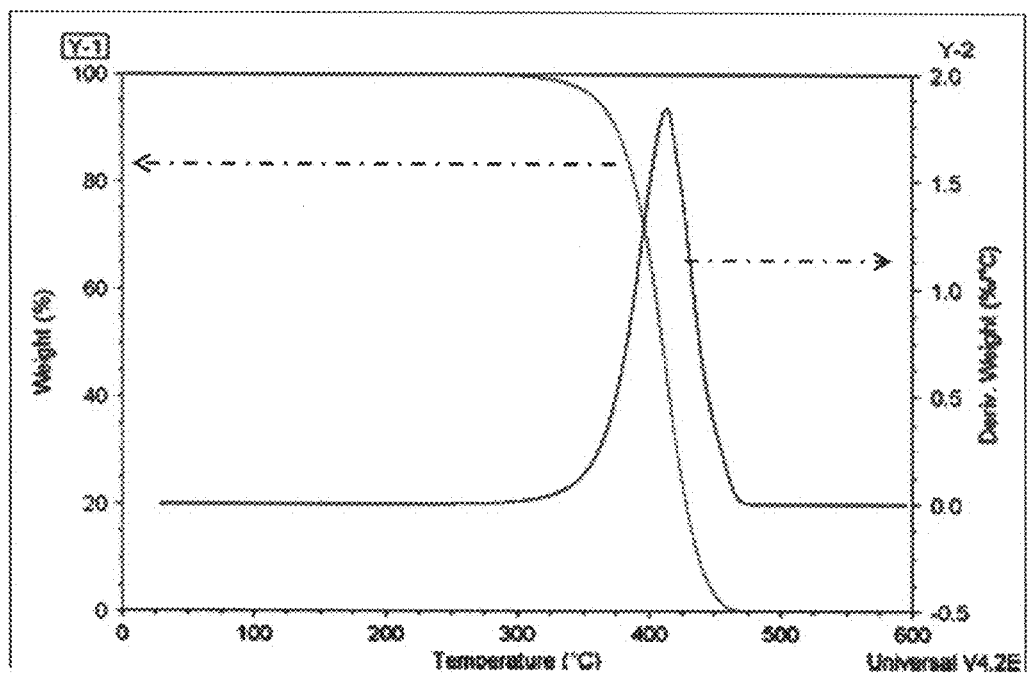
FIG. 2: Thermogram showing the thermal degradation profile of soybean oil (used as an example lipid) as a function of temperature. The curve corresponding to the primary y-axis (left) shows the decrease in absolute sample weight (as percentage of initial mass) as a function of temperature. The curve corresponding to the secondary y-axis (right) shows the derivative of the weight loss with respect to temperature. A peak on this curve indicates the temperatures zone where the relative magnitude of weight loss is more significant than the flat parts of the curve. The axes corresponding to each curve are indicated by dashed arrows on the figure.
Figure 12:
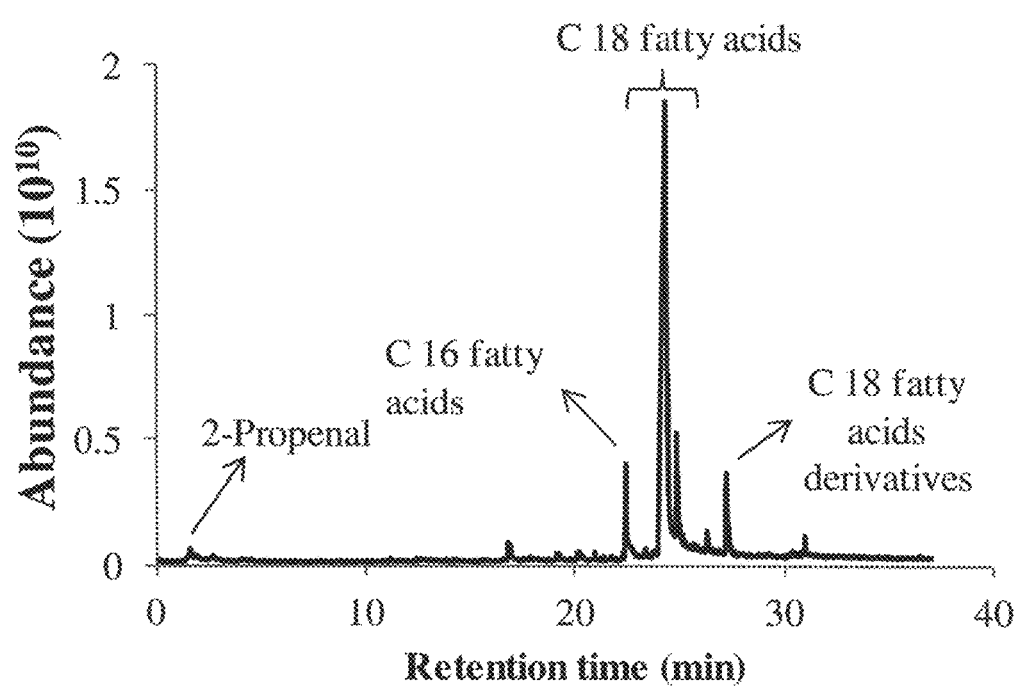
FIG. 12: GC-MS chromatogram of products from pyrolysis of soy oil at 420° C.

Most triglyceride pyrolysis, however, occurred at much higher temperatures (>380° C., FIGS. 1-2). When pyrolyzed at 420° C., soy oil produced large quantities of C16 and C18 fatty acids as well as hydrocarbons such as tetradecane, pentadecane, 8-heptadecene, heptadecane, and 9,12-octadecadien-1-ol (FIG. 12), confirming the extensive cleavage of the glyceride ester bonds as well as partial decarboxylation during the thermal degradation process.

Figure 13A:
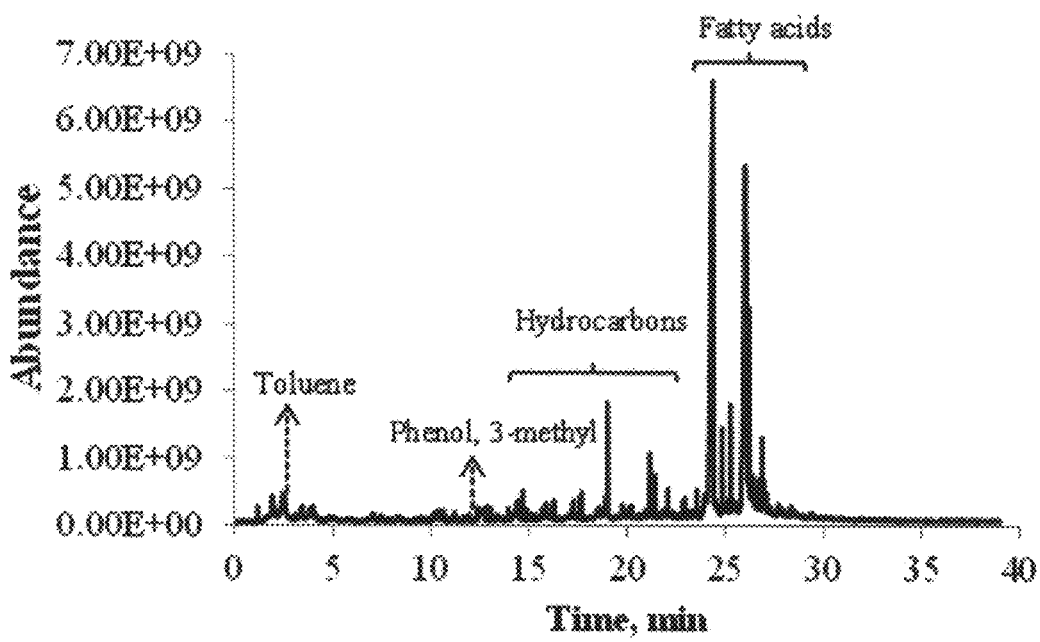
FIGS. 13A-13B: GC-MS chromatogram of bio-oils formed during isothermal heating at 420° C. from *Chlorella* sp.
Figure 13B:
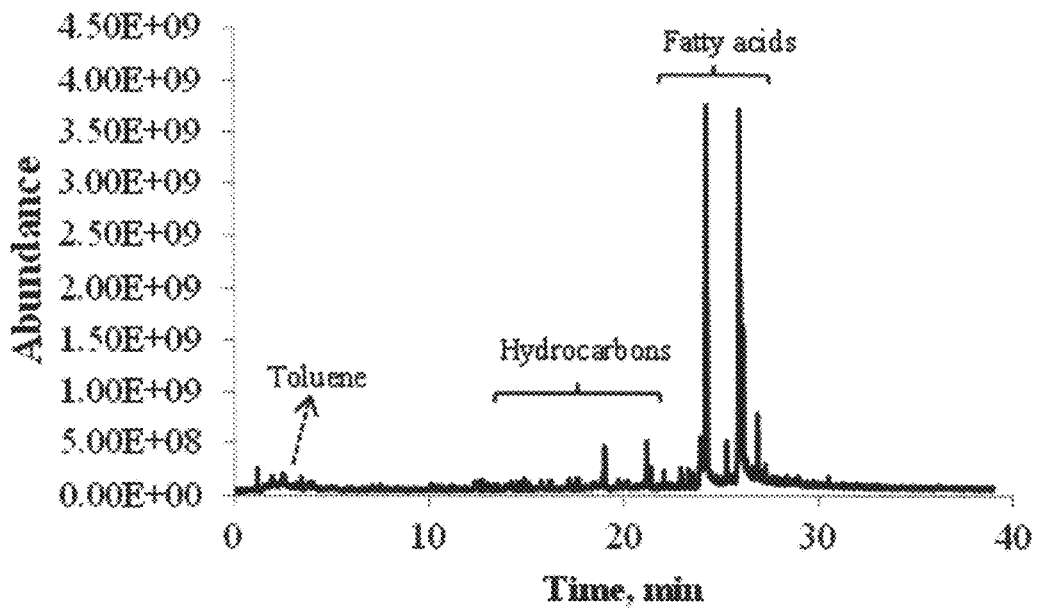

Accordingly, in the second step of pyrolytic fractionation, solid residues from the algae samples left behind from the previous step (at 320° C.) were heated at 420° C. Similar to soy oil pyrolysis products, the primary products for all the biomass samples were observed to be C16-C18 fatty acids and alkanes such as tetradecane, pentadecane, 8-heptadecene, heptadecane (FIGS. 13A-13B, Table 3 (FIG. 14) and Table 4 (FIG. 15)). Only a small C16 fatty nitrile peak was seen in the Chlorella sp. chromatogram, but no N-compounds were discernible in the products from Scenedesmus sp. samples pyrolyzed at 420° C. Without wishing to be bound by theory, it is possible that N-derivatives of fatty acids were formed as a result of reactions of the free fatty acids (produced in this step due to breakdown of triglycerides) with polymerized (charred) proteins from the previous pyrolysis steps. Since fatty nitriles have been considered as fuel additives to improve lubricating properties, the presence of these compounds at low concentrations, in fact, enhances the fuel value of triglyceride-derived bio-oil from pyrolytic fractionation. Trace amounts of toluene and 4-methyl-phenol were also observed in triglyceride-based bio-oils from both the oleaginous algal feedstocks and could have formed from degradation of recalcitrant or charred proteins.

Example 3: Lab-Scale Pyrolysis

Figure 16:
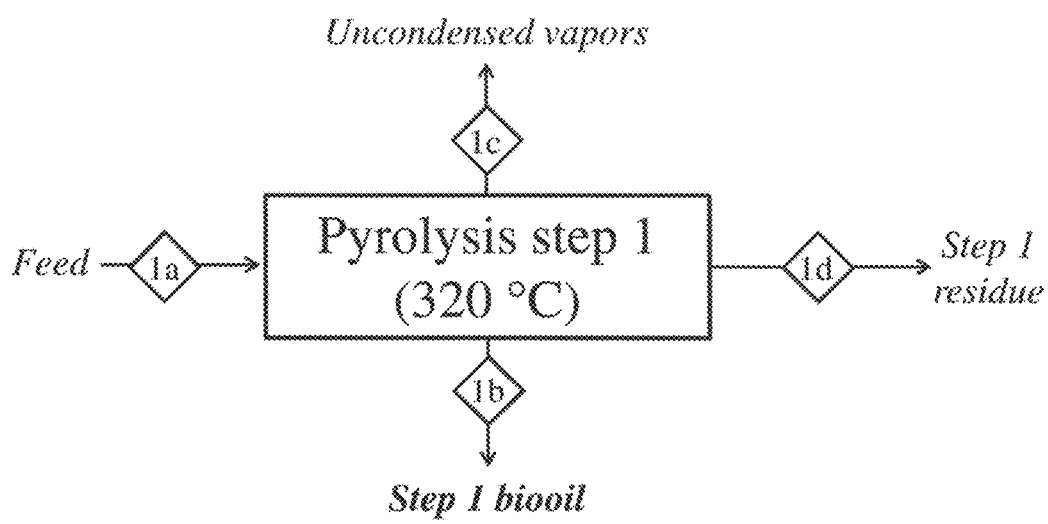
FIG. 16: Total and component mass balance data obtained from bench-scale fixed-bed experiments for Step 1 pyrolysis of oleaginous *Chlorella* sp. at 320° C. †indicates lipid is quantified as FAMEs; ‡ indicates lipid is sum of hydrocarbons, free fatty acids, fatty amides, and fatty nitrile; * indicates lipid is triglycerides.

To validate the scalability of observations made from micro-pyrolysis experiments for production of triglyceride-specific bio-oils, larger scale fixed bed pyrolytic fractionation tests were performed using oleaginous *Chlorella* sp. These experiments were performed under "fast pyrolysis" mode with a vapor residence time approximately 2 s. Biomass was first pyrolyzed at 320° C. (Step 1) using 9.33 g of biomass with a total lipid content of 27% (g-lipid/g-biomass) (measured as total fatty acid methyl ester (FAME)). The majority of the lipids were measured to be triglycerides (TAG) (23% g-TAG/g-biomass) and the remaining small fraction (4% g-lipid/g-biomass) was likely composed of membrane lipids and cellular free fatty acids. Mass balance data for Step 1 pyrolysis (at 320° C.) is shown in FIG. 16. The bio-oils produced in this step contained several protein and carbohydrate derived products including levoglucosans and N-compounds (see FIGS. 6A-6B and FIG. 18). In addition, a small amount of fatty acids were also produced, likely from the more thermally labile cellular lipids. However, the vast majority of lipids, likely triglycerides, were not pyrolyzed during Step 1 and remained associated with the residue from this step (see lipid balance data in FIG. 16 quantified using GC-FID analysis of bio-oil samples and solid residues). Nearly 25% of the biomass N was also removed in Step 1 (see nitrogen balance data in FIG. 16).

Figure 19:
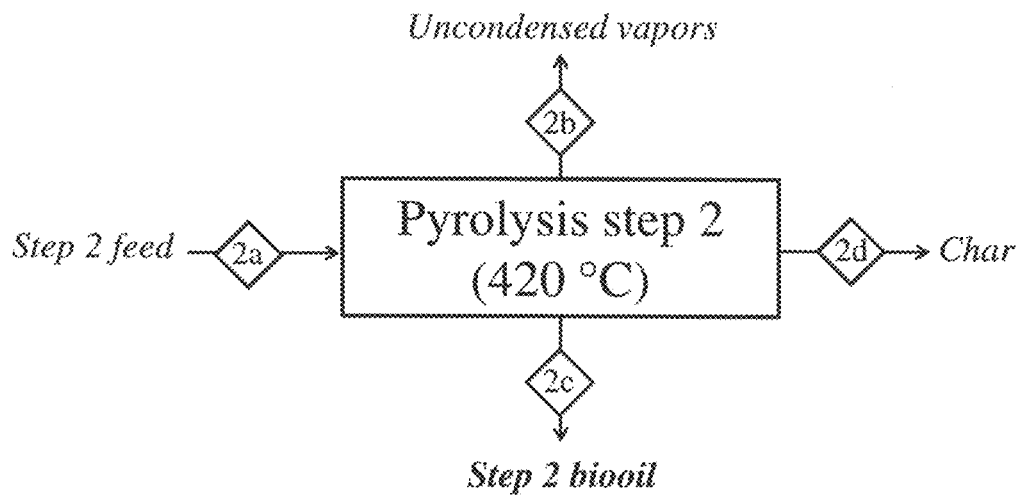
FIG. 19: Total and component mass balance data obtained from bench-scale fixed-bed experiments for Step 2 pyrolysis of oleaginous *Chlorella* sp. at 420° C. Step 2 was performed on residues from pyrolysis Step 1 (stream 1d from FIG. 16). Vindicates lipid is quantified as FAMEs; indicates lipid is sum of hydrocarbons, free fatty acids, fatty amides, and fatty nitrile.
Figure 20:
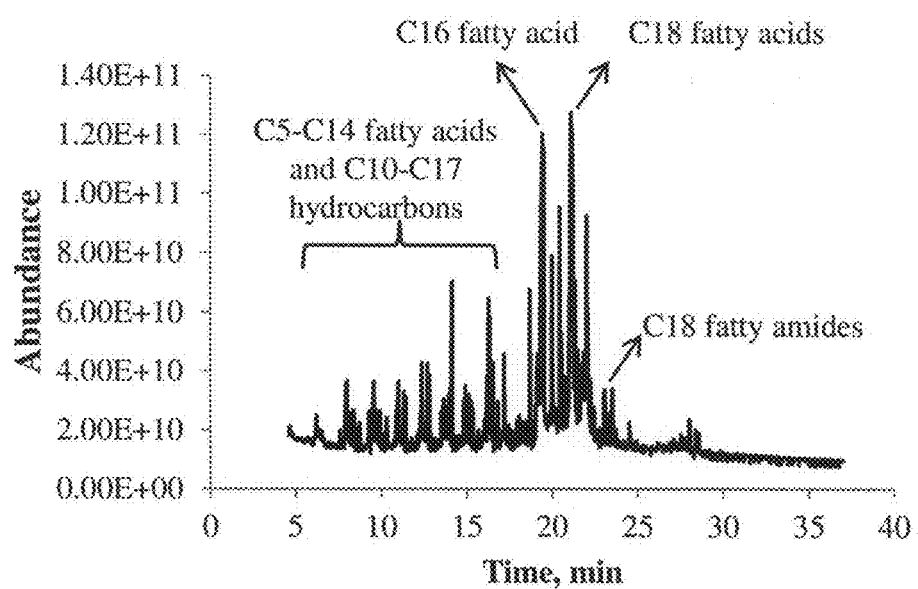
FIG. 20: GC-MS chromatogram of bio-oil collected from Step 2 of fixed-bed pyrolytic fractionation performed on oleaginous *Chlorella* sp. at 420° C. 5.0 mg of bio-oil was dissolved in 1 mL of chloroform for analysis.
Figure 22:
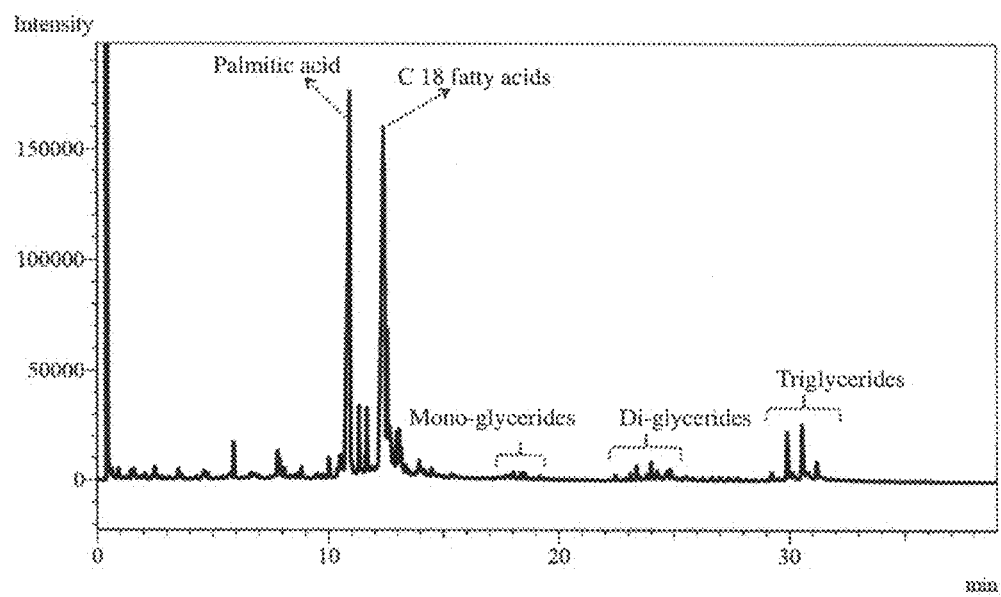
FIG. 22: GC-FID chromatogram of bio-oil collected from Step 2 of fixed-bed pyrolytic fractionation performed on oleaginous *Chlorella* sp. at 420° C.
Figure 23:
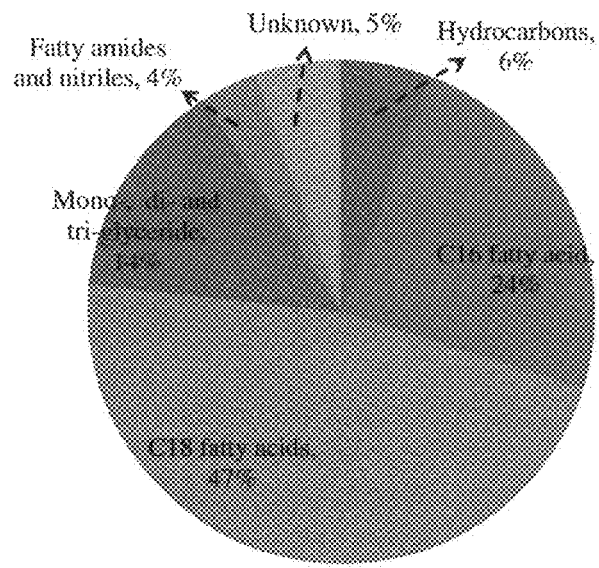
FIG. 23: Mass fractions of the components in bio-oil collected during Step 2 of bench-scale fixed-bed pyrolytic fractionation experiments with oleaginous *Chlorella* sp. at 420° C.

The residue from Step 1 was subjected to a second pyrolysis reaction at 420° C. (Step 2). The second step at 420° C., targeted towards triglyceride pyrolysis, produced bio-oil largely composed of fatty acids and glycerides. In addition, small amounts of hydrocarbons and fatty amides were also produced (see GC-MS chromatogram in FIG. 20, identified products in FIG. 21, and GC-FID chromatogram in FIG. 22). Quantification of bio-oil constituents through correlation of GC-FID peak areas with corresponding calibration standards for all detected compounds shows that nearly 95% of the recovered mass are attributed to lipid-derived products, most likely obtained from thermal degradation of triglycerides (see total mass and lipid-derivative mass data for stream 2b in FIG. 19 and mass fraction of bio-oil components in FIG. 23). The lipid mass balance data for step 2 (FIG. 19) also shows that nearly 94% of the lipid mass fed to step 2 (stream 2a) was recovered in the bio-oil (stream 2b). Although some N was also present in Step 2 bio-oil, N-balance analysis across both Steps 1 and 2 indicates that <15% of N present in biomass was recovered in liquid products in Step 2. In contrast, previous studies have reported that nearly 60% of biomass N is accumulated in bio-oil after a single-step pyrolysis.

The calorific value of triglyceride-specific bio-oil from step 2 was calculated to be approximately 41 MJ/kg (Table 7, FIG. 24) and is similar to higher heating values of petro diesel (42 MJ/kg). Overall, lab-scale pyrolytic fractionation experiments demonstrated that triglyceride-specific bio-oils with low N-content and high calorific value can be produced from oleaginous biomass via pyrolytic fractionation. Also, since pyrolytic fractionation produces fatty acid vapors, it is possible to synthesize fuels (e.g. biodiesel) and chemicals (oleo-chemicals such as fatty amides and fatty nitriles) through gas-phase reactions of fatty acids.

Example 4: Process Design

Figure 25:
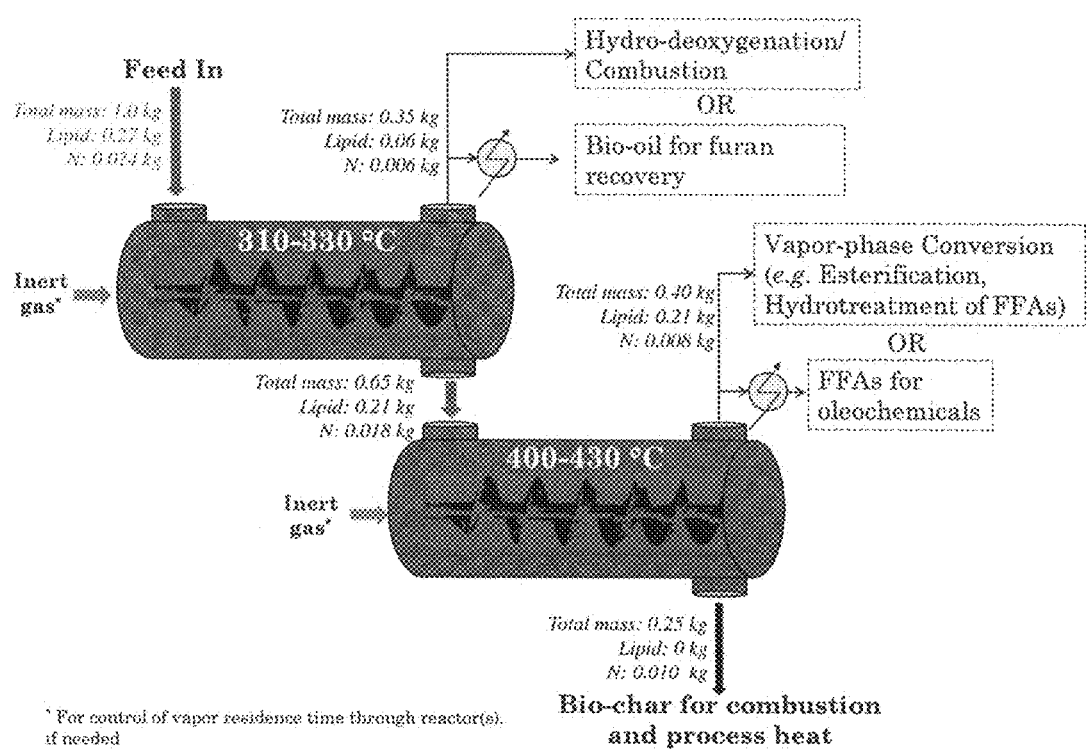
FIG. 25: Non-limiting process design of a pyrolytic fractionation system showing mass balances and product pathways to fuels and co-products.

FIG. 25 shows a pyrolytic fractionation process flow diagram with two reactors that are sequentially maintained at temperatures of 320° C. and 420° C. to volatilize protein as well as carbohydrate, and triglycerides. Based on results from the TG and Pyroprobe™ experiments described above, the solids in each reactor have a residence time of approximately 10 min to achieve near-complete pyrolysis. However, the vapor residence time can be maintained to be much lower (a few seconds) to prevent secondary gas-phase degradation reactions by flow of additional inert gases (to sweep out the vapors), thus accomplishing independent control of solid and vapor residence times.

This process design offers several advantages relative to fluidized bed reactors. Low (or no) flow of inert gas may be important in this system since fluidization of solids is not needed. Also, since the pyrolysis steps in the two-step process are carried out at much lower temperatures (<450° C.) than more traditional single-step pyrolysis (>550° C.), secondary gas-phase reactions are likely to be much slower. As a result, maintaining very short vapor residence times (<1 s, typical of fast pyrolysis) by using high flow rates of inert gas may not be necessary to achieve high yields of bio-oil. In fact, when reactors are operated at high solid, the pressure of the generated vapors may itself be sufficient to impart gas velocities required to prevent secondary reactions. Thus, the costs associated with heating the carrier gas and subsequent energy recovery can be minimized or eliminated. Additionally, if solids are not fluidized, cyclones are not needed for solids recovery and vapor product condensation. This results in enhanced efficiency since concentrations of condensable vapors are higher in the absence of non-condensable inert gases. Char blow-out and subsequent contamination of bio-oils can also be avoided.

In the process scheme shown in FIG. 25, bio-oils from the first reactor (protein as well as carbohydrate pyrolysis) are processed to recover high value N-compounds such as indole and pyrimidine and oxygenated compounds (furan compounds). The bio-oil vapors from the first reactor can be directly integrated with a hydro-treatment system to produce drop-in green gasoline. Furans (and derivatives) can also be recovered as higher value products. The triglyceride-rich residue is pyrolyzed in a second reactor to produce and recover fatty acids. Alternately, the fatty acid vapors can be directly converted to fatty acid methyl esters (FAMEs) or alkanes via vapor-phase reactions. Finally, char is combusted for process heat, or used as soil amendment or to recover nutrients for re-use in algal cultivation.

Using a process scheme such as the one shown in FIG. 25, the net energy requirements of the process would be similar to those for alternate hydrothermal liquefaction processes, and could be further lowered if appropriately integrated with other industries that produce waste low-grade heat.

Figure 26:
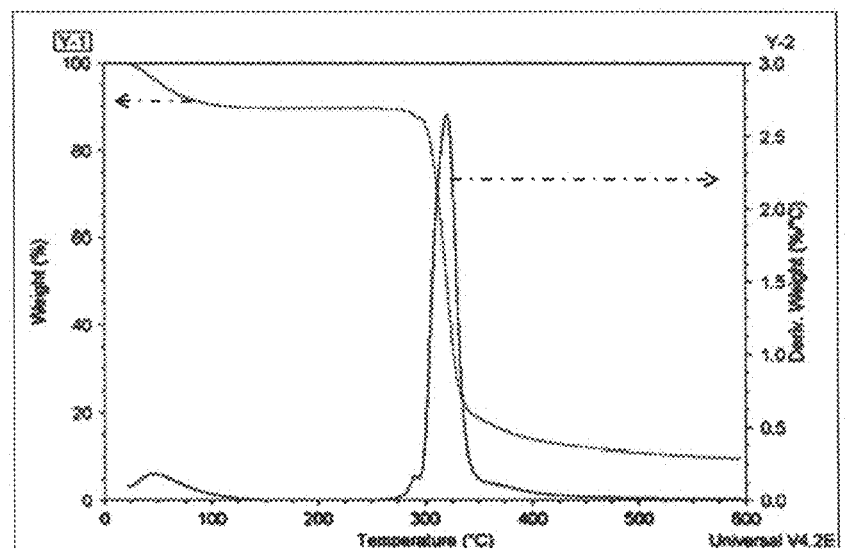
FIG. 26: Thermogram showing the thermal degradation profile of corn starch (used as an example carbohydrate) as a function of temperature. The curve corresponding to the primary y-axis (left) shows the decrease in absolute sample weight (as percentage of initial mass) as a function of temperature. The curve corresponding to the secondary y-axis (right) shows the derivative of the weight loss with respect to temperature. A peak on this curve indicates the temperatures zone where the relative magnitude of weight loss is more significant than the flat parts of the curve. The axes corresponding to each curve are indicated by dashed arrows on the figure.

Example 5: Thermal Degradation Temperature Ranges for Illustrative Carbohydrates In this example, it is shown that carbohydrates degrade over temperature range of 300-350° C. FIG. 26 shows the TGA profile for corn starch, an example carbohydrate, which volatilizes between 300° C. and 350° C. FIG. 2 shows the results of the thermogravimetric analysis of soy oil, an example lipid. Lipids degrade at a much higher temperature of 370° C. to 480° C. These thermograms clearly establish that proteins, carbohydrates, and lipids undergo pyrolysis in distinct, non-overlapping temperature regimes.

Example 6: Thermal Fractionation of a Carbohydrate-Rich Green Alga (*Scenedesmus* sp.)

This species of fast-growing microalgae was grown in an outdoor photobioreactor. It was determined that 25% (w/w) of *Scenedesmus* sp. was protein, 40% (w/w) was starch, 8% (w/w) was lipid, and the remaining was ash and other minor biopolymers (such as sterols, phytols, etc.). The proximate analysis (Table 8) of this biomass shows that nearly 60% of the carbon can be volatilized.

TABLE 8

Proximate analysis of *Scenedesmus* sp.

| | |
|---|---|
| Moisture content (wt %) | 2.2 |
| Volatile matter (wt %) | 59.2 |
| Fixed carbon (wt %) | 20.7 |
| Ash (wt %) | 17.9 |

Figure 27:
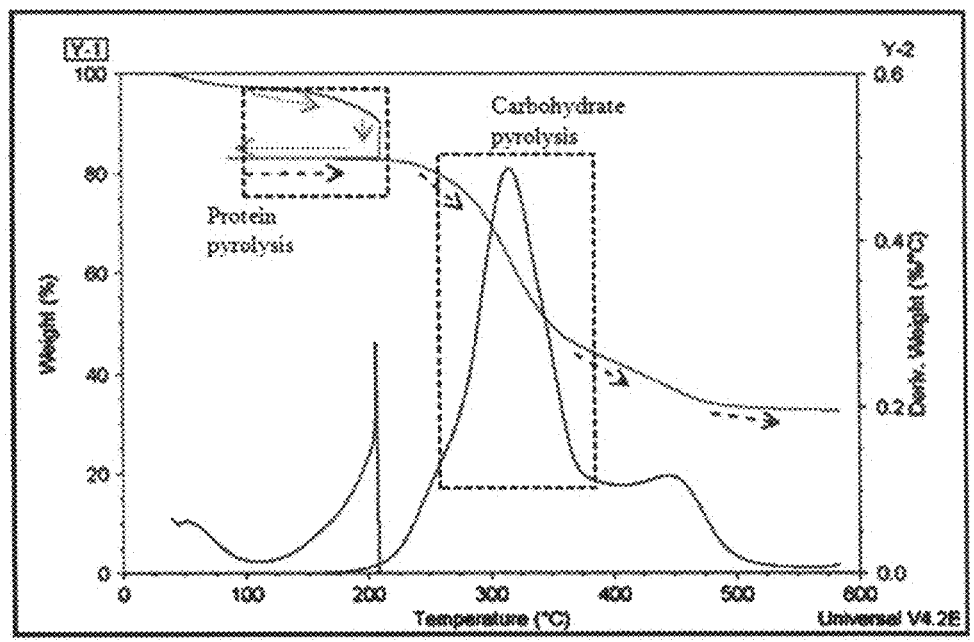
FIG. 27: Thermogram showing separate volatilization of the protein and carbohydrate fraction with *Scenedesmus* sp. upon application of a "thermal fractionation protocol." The arrows indicate the sequence of temperature events for this sample—(i) initial heating to 210° C.; (ii) hold at 210° C. until volatilization of the protein fraction is complete; (iii) cooling down and reheating sample to verify absence of peak at 210° C.; and, (iv) re-heating to volatize carbohydrates.

Thermogravimetric analyses of dry *Scenedesmus* sp. samples are shown in FIG. 27. In this experiment, temperature was continuously increased to 600° C. at fixed rate of 10° C./min. Three distinct peaks were seen in these TGA profiles at 220° C., 300° C., and 450° C. Based on the data from Example 5, these peaks are attributed to the pyrolysis of protein, carbohydrate, and lipid, respectively. The observations for pure model compounds correlate well with a biomass that comprises these biopolymers. Moreover, the temperature windows of each component are reasonably well separated to enable separate recovery of the pyrolysis products corresponding to each biopolymer class.

Based on the TGA profile in FIG. 1B, the thermal fractionation of *Scenedesmus* sp. was carried out using the following protocol (called "thermal fractionation protocol" hereafter):

Initially, the temperature of a *Scenedesmus* sp. sample was increased up to 210° C. This temperature was maintained for 10 min by which time no further weight loss was observed, indicating that protein pyrolysis was complete. This was verified by then cooling the samples back to room temperature and re-heating (see boxed region marked "protein pyrolysis" in FIG. 27 and the arrows in the box).

In this second stage heating, the peak corresponding to protein at 220° C. is absent (compare the derivative weight loss profiles in FIG. 1B and FIG. 27), confirming the removal of pyrolyzable proteins. Thereafter, further heating resulted in pyrolysis of starch at 300° C., indicating that the removal of protein and the prolonged exposure to the lower temperatures did not have any effect on the carbohydrate fraction (peaks are at similar temperatures in FIG. 26 and FIG. 27).

Thus, removal of pyrolyzable protein leaves behind a biomass fraction that is largely carbohydrate. The bio-oil resulting from the pyrolysis of this residue is essentially N-free and is hence of higher quality than the bio-oil from pyrolysis of the original feedstock.

Example 7: Thermal Fractionation of Soy Bean Flour Containing Protein, Carbohydrate, and Lipid Soy flour was chosen as an example feedstock to demonstrate thermal fractionation of biomass that contains all three major non-lignin biopolymers—proteins, carbohydrates, and lipids. As such, this approach is also applicable to oleaginous algae.

Figure 28:
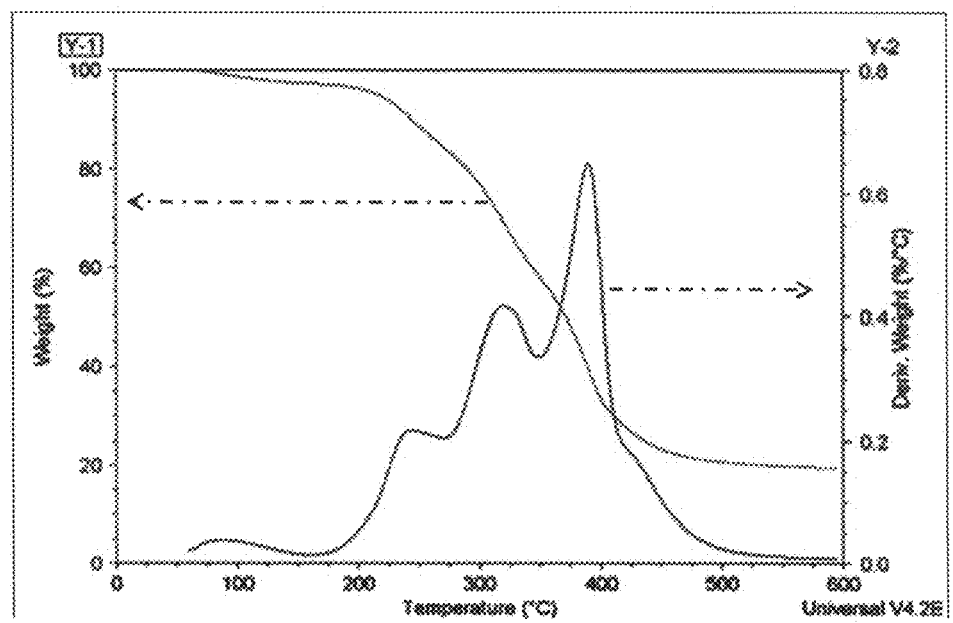
FIG. 28: Thermogram showing the thermal degradation profile of soybean flour (used as an example biomass that contains protein, carbohydrate, and lipids) as a function of temperature. The curve corresponding to the primary y-axis (left) shows the decrease in absolute sample weight (as percentage of initial mass) as a function of temperature. The curve corresponding to the secondary y-axis (right) shows the derivative of the weight loss with respect to temperature. A peak on this curve indicates the temperature zone where the relative magnitude of weight loss is more significant than the flat parts of the curve. The axes corresponding to each curve are indicated by dashed arrows on the figure.

Similar to Example 6, traditional pyrolysis was first carried out using a constant heating rate of 10° C./min. This TGA profile is shown in FIG. 28. Three peaks can be seen at 250° C., 320° C., and 400° C.—each corresponding to protein, starch, and lipid within the temperature windows identified in Example 5.

Figure 29:
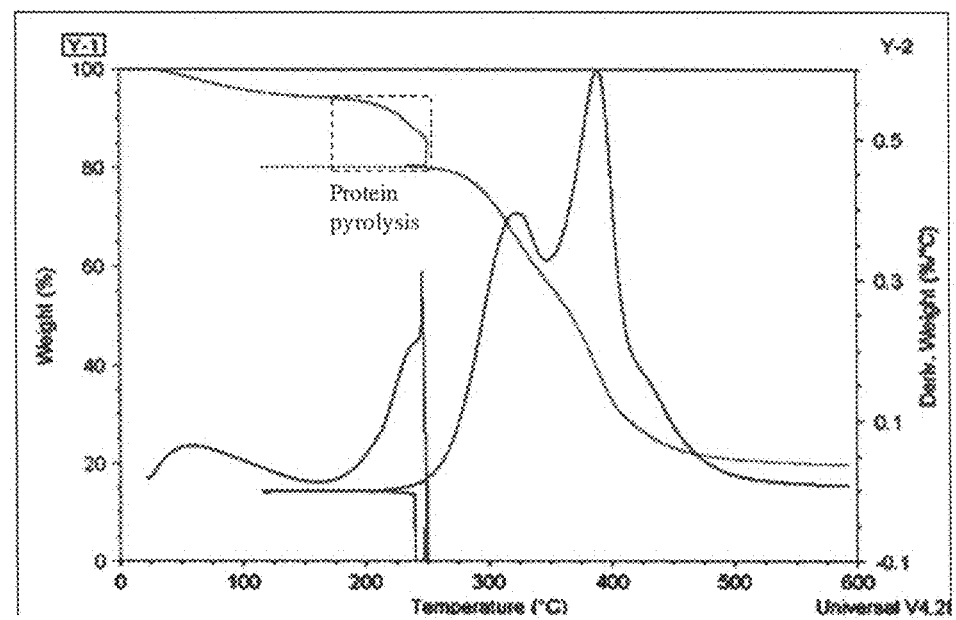
FIG. 29: Thermogram showing volatilization of the protein fraction alone from soybean flour (used as an example biomass that contains protein, carbohydrate, and lipids) upon application of a "thermal fractionation protocol." The removal of protein at the lower temperature does not influence the thermal properties of the remaining biopolymers—carbohydrate and lipid.

For this feedstock, the thermal fractionation protocol was implemented twice—first to pyrolyze proteins, and then to pyrolyze starch. As seen in FIG. 29, heating up to 250° C. followed by isothermal heating at this temperature for 10 min resulted in protein pyrolysis. Subsequent cooling of the sample back to 45° C. and reheating confirmed the complete removal of pyrolyzable proteins. Further heating to 320° C. and maintaining isothermal conditions resulted in pyrolysis of starch. As before, cooling the sample back to 45° C. and reheating showed that the starch fraction was also removed, along with protein (FIG. 30).

Figure 30:
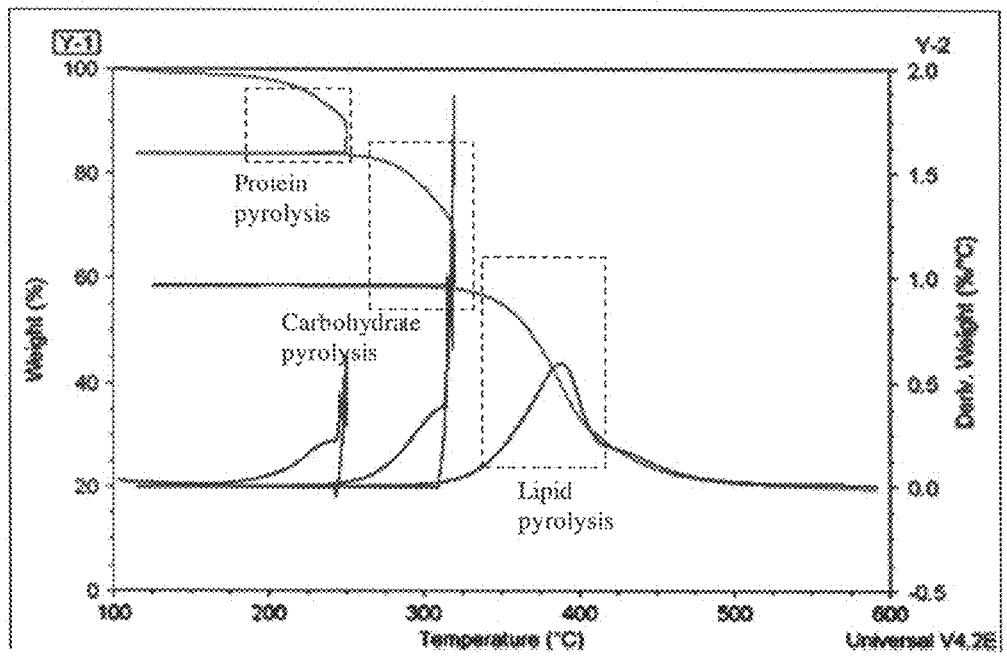
FIG. 30: Thermogram showing volatilization and separate recovery of the protein, carbohydrate, and lipid from soybean flour (used as an example biomass that contains protein, carbohydrate and lipids) upon application of a "thermal fractionation protocol."

Further heating beyond 320° C. resulted in volatilization and pyrolysis of the triglyceride (lipid) fraction (also shown in FIG. 30). Thus, for biomass that contains protein starch and lipids, a thermal fractionation approach is useful to derive component-specific bio-oils that have a higher degree of homogeneity and therefore facilitate the production of multiple high grade fuels upon subsequent processing, as described below.

Example 8: Conversion of Triglycerides to Free Fatty Acids Upon Volatilization

The above examples demonstrated that triglycerides from soy oil are decomposed into their constituent free fatty acids upon heating to temperatures slightly above their boiling point (370° C.) followed by rapid re-condensation to near-ambient temperatures. In these experiments, soy oil was heated in a round bottom flask that was connected to an overhead condenser cooled with ice-cold water. The soy oil-containing flask was maintained at a constant temperature of 370° C. An inert atmosphere was maintained in the system by continuous purging with nitrogen. Nitrogen also served as the carrier gas for the vapors and based on gas flow rates used. The residence time of the hot vapors was less than 5 s, resulting in conditions of fast-pyrolysis. Composition of the initial oil, condensed vapors, and residual oil was measured using gas chromatography (GC) techniques with the aid of a flame ionization detector (FID). A Restek Biodiesel capillary column was used to separate the various lipid components.

Figure 31:
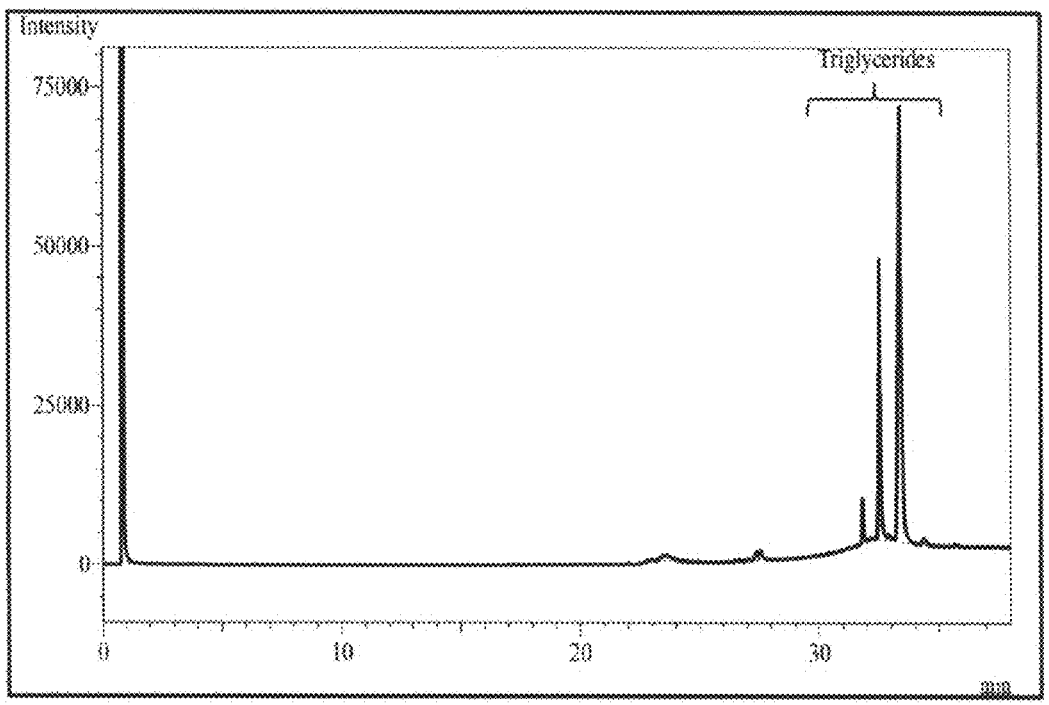
FIG. 31: Gas chromatograph of untreated soy oil (used as an example lipid) showing that the majority of the lipids are in the form of triglycerides eluting between 30-35 min.
Figure 33:
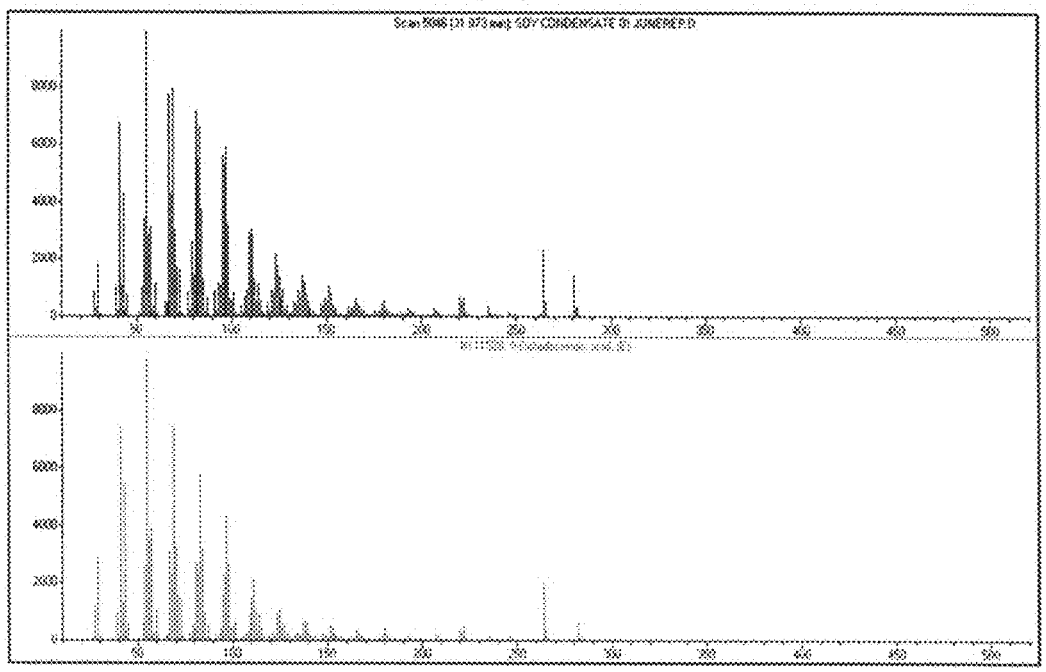
FIG. 33: Mass spectrograph of soy oil (used as an example lipid) condensate confirming production of oleic acid as one major product of the thermal treatment.
Figure 34:
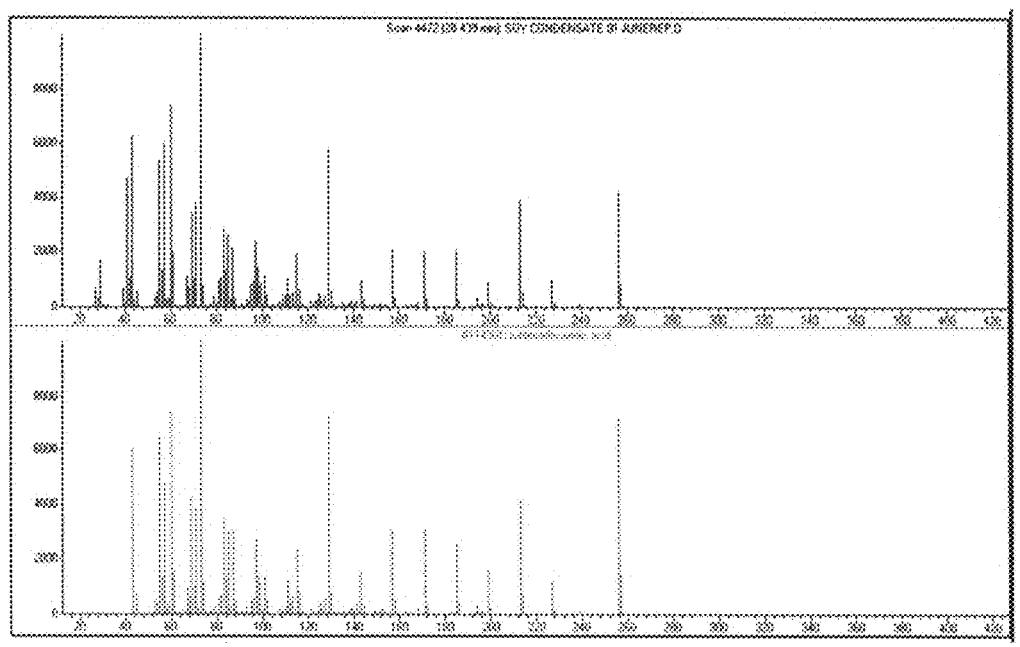
FIG. 34: Mass spectrograph of soy oil condensate confirming production of hexadecanoic acid as the second major product of the thermal treatment.

FIG. 31 shows that the lipids in the soy oil feedstock were primarily triglycerides eluting between 30-35 min. However, after the low-temperature pyrolysis, nearly all the triglycerides were converted into shorter-chain fatty acids or hydrocarbons, as shown in the GC chromatogram of the condensate in FIG. 32 and confirmed by the mass spectrometry (GC-MS) results shown in FIG. 33 and FIG. 34.

Figure 32:
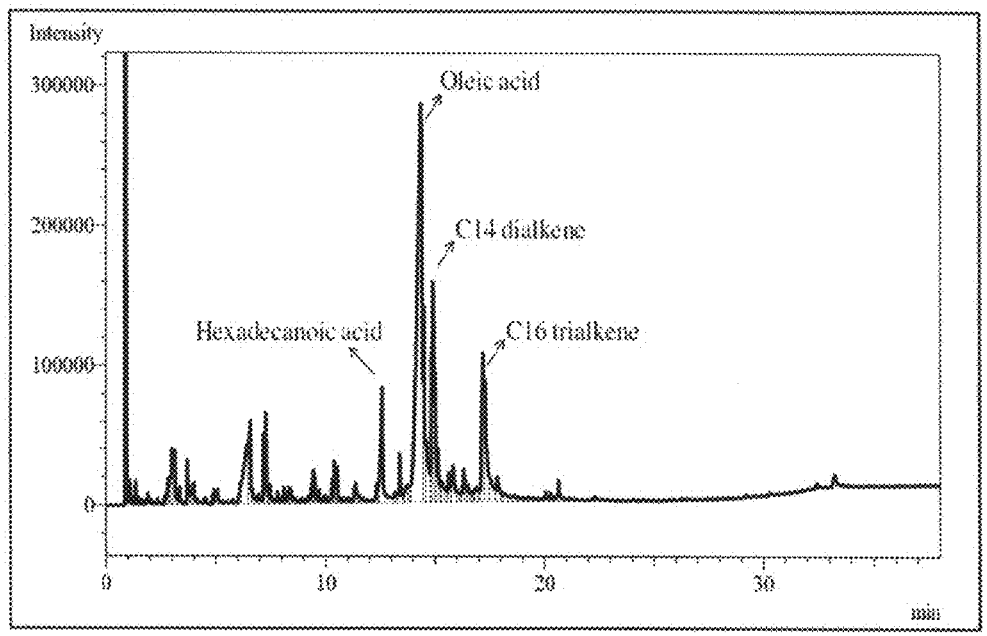
FIG. 32: Gas chromatographs of soy oil (used as an example lipid) subjected to isothermal heating at 370° C. followed by condensation of the vapors. These results show conversion of the native triglycerides to lower molecular weight fatty acids and hydrocarbons.

Soy oil primarily contains triglycerides comprising oleic (C18:1, ~23%), linoleic (C18:2, ~51%), α-linolenic acid (C18:3, ~7-10%), palmitic acid (C16:0, 10%), and stearic acid (C18:0, 4%) side chains. The data in FIG. 32 shows that vaporization and rapid cooling results in formation of free oleic acid, hexadecanoic acid, decenoic acid, and hydrocarbons such as C14 dialkene and C16 trialkene.

Figure 35:
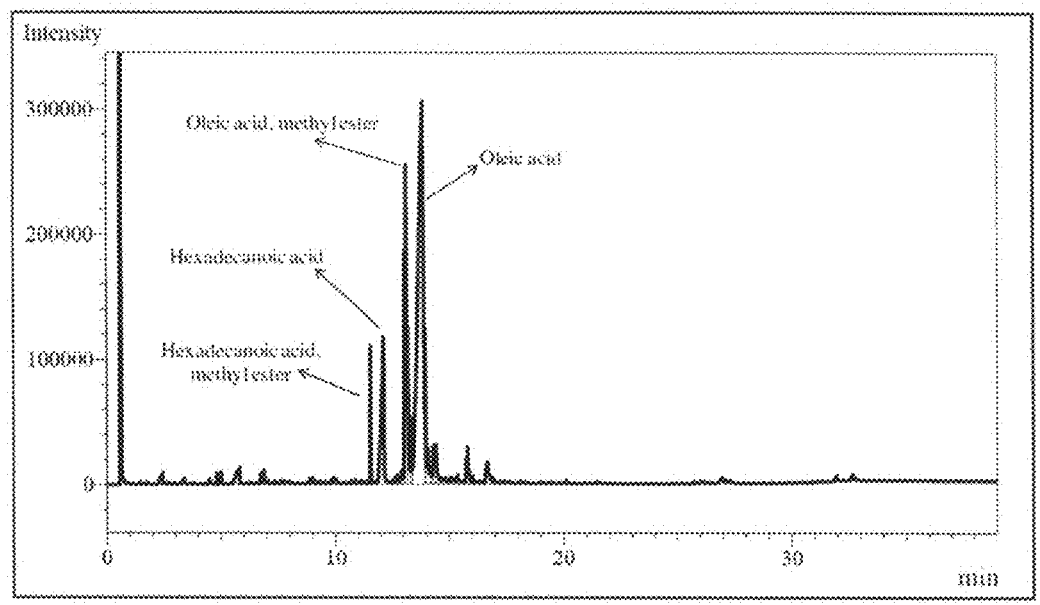
FIG. 35: Gas chromatograph of the product mixture resulting following non-catalytic vapor phase reaction between soy oil and methanol vapors.
Figure 36:
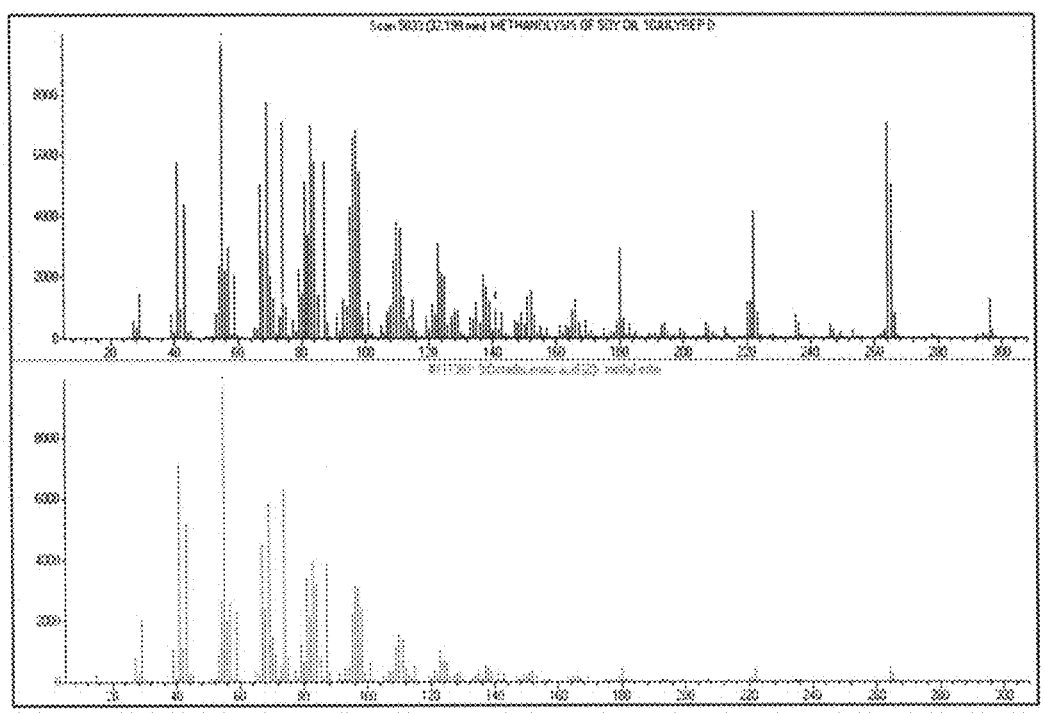
FIG. 36: Mass spectrograph of condensate from vapor phase reaction confirming production of oleic acid methyl ester.
Figure 37:
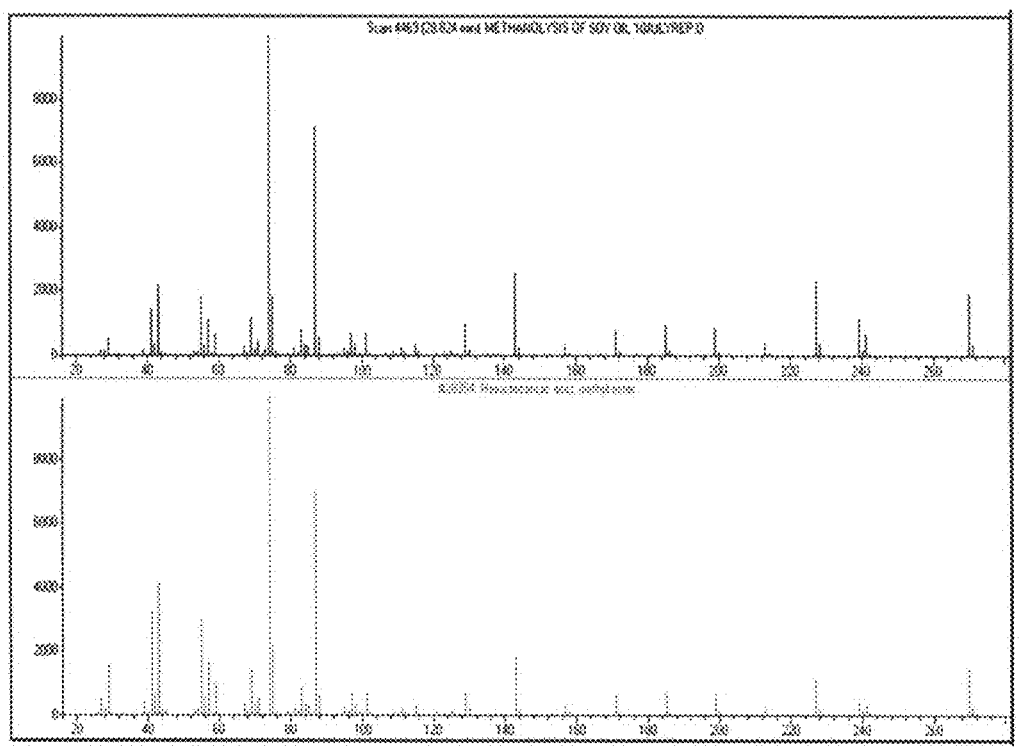
FIG. 37: Mass spectrograph of condensate from vapor phase reaction confirming production of hexadecanoic acid methyl ester.

Example 9: Vapor Phase Esterification of Free Fatty Acids to Methyl Esters without the Use of a Catalyst This example shows that free fatty acids can be easily converted into fatty acid methyl esters (FAMEs, the primary constituent of biodiesel) through simple vapor-phase esterification with methanol (see FIGS. 35, 36, and 37). Unlike conventional esterification reactions which require a catalyst and up to an hour or longer reaction times, the method used herein accomplishes the same reaction within a few seconds without needing any catalyst. In the example shown, the reaction time was about 5 s and about 40% yield of the ester products was obtained.

Further, since esterification is an endothermic reaction, the higher temperatures result in an increase in the equilibrium constant of the reaction. Thus, under these reaction conditions, addition of large excess reactant alcohol is not required to achieve high conversions—which is a common practice in traditional acid or base catalyzed transesterification.

In addition, traditional biodiesel production from oleaginous biomass (such as lipid-rich algae) requires several processing steps of lipid extraction, acid or base catalyzed transesterification, as well as solvent- and catalyst-recovery. In contrast, the method described herein eliminates the need for these multiple unit operations. If required, solid acid catalysts can easily be incorporated into this process such as by passing the reactant vapors through catalyst beds. Such catalysts are commercially available and stable over long periods without deactivation. Process steps associated with recovery of soluble homogenous catalysts are eliminated by this approach, thereby lowering process costs. Product purification steps can also be minimized or even eliminated with the method described herein since the product predominantly consists of hydrocarbons. (In contrast, traditional biodiesel production often requires washing of the transesterified lipids with water to remove impurities, such as glycerol, that affect engine performance and life.)

Similar to the FAMEs production described above, free fatty acid (FFA) vapors can serve as a platform substrate that can also be converted to fatty alcohols, value-added oleochemicals, and drop-in fuels through facile vapor-phase chemical transformations.

Overall, use of this thermal fractionation approach to non-ligninaceous biomass results in conversion of a greater fraction of feedstock carbon into fuels. Since each biopolymer is converted separately, efficient fuel upgradation steps tailored to biopolymer-specific oils can be accomplished using the method described herein. The biomass nitrogen can be contained to only one fraction of the overall bio-oil, thereby resulting in higher quality fuels from the rest of the material. For oleaginous biomass, the bio-oil from the lipid fraction, after online vapor-phase esterification, can be used directly with minimal, if any, further purification or processing.

Example 10: Production of Upgraded Bio-Oils by Continuous in-Line Hydrogenation of Pyrolysis Vapors (Hydropyrolysis)

Experiments were performed where the pyrolysis vapors were subjected to continuous hydrogenation. These experiments confirmed that deoxygenated hydrocarbon products (suitable as direct petroleum fuel replacements) can be produced by this method. These experiments were carried out with three separate algae species—(a) *Ankistrodesmus* sp., (b) *Scenedesmus* sp., and (c) *Cladophora* sp.—to confirm the applicability of this method to a wide variety of algal biomass types. The experiments were performed in a Pyroprobe 5200 pyrolysis GC mass spectrometer (Py-GC/MS) (CDS Analytical, Oxford, Pa.) that was also equipped with an inline high pressure fixed bed catalytic reactor (containing Pt catalyst) for continuous hydrogenation of the pyrolyzed vapors. Four experiments were carried out ((i) through (iv), Table 9) with each algal sample at varying $H_2$ pressures and catalytic bed temperatures to demonstrate the progressive effectiveness of the inline hydrogenation method for production of hydrocarbon fuels with increasing severity of operating conditions.

TABLE 9

Experimental conditions for hydropyrolysis experiments

| Experiment # | Pyrolysis temp. (° C.) | Hydrogenation reactor temp. (° C.) | Hydrogen pressure (psi) |
|---|---|---|---|
| (i) | 600 | 50 | 0[†] |
| (ii) | 600 | 50 | 20 |
| (iii) | 600 | 300 | 100 |
| (iv) | 600 | 400 | 300 |

[†]Helium used as purge gas at atmospheric pressure

The pyrolysis reactor was set at 600° C. for all experiments. Results of these experiments ((i) through (iv)) for *Ankistrodesmus* sp., *Scenedesmus* sp., and *Cladophora* sp are shown in FIGS. 38, 39, and 40, respectively.

Figure 38:
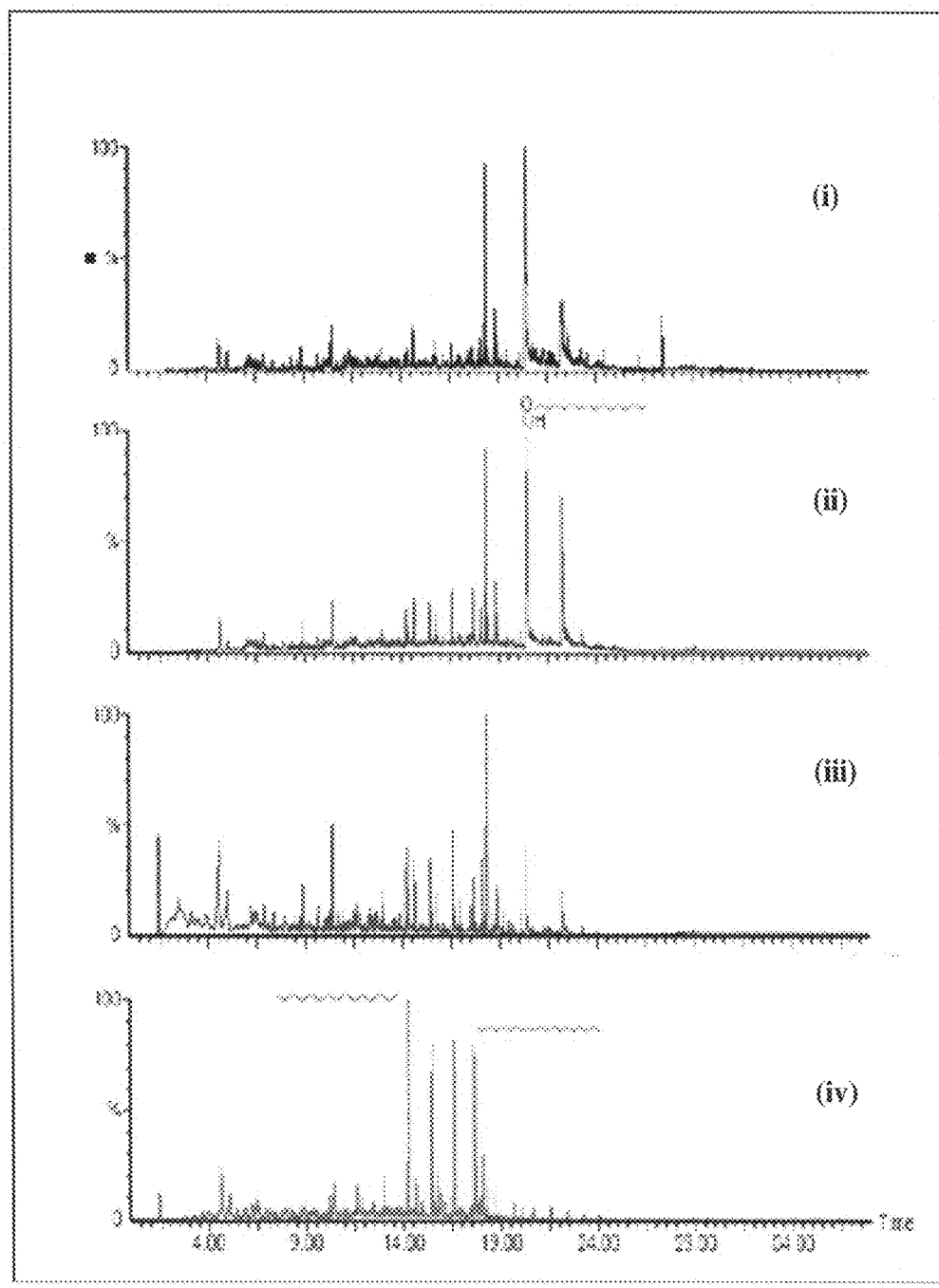
FIG. 38: Gas chromatograph of products resulting from thermal treatment of *Ankistrodesmus* sp. in the absence and presence of hydrogen. Some compounds are indicated in the figure to show progressive deoxygenation and hydrogenation of the bio-oil products with increasing treatment severity.
Figure 39:
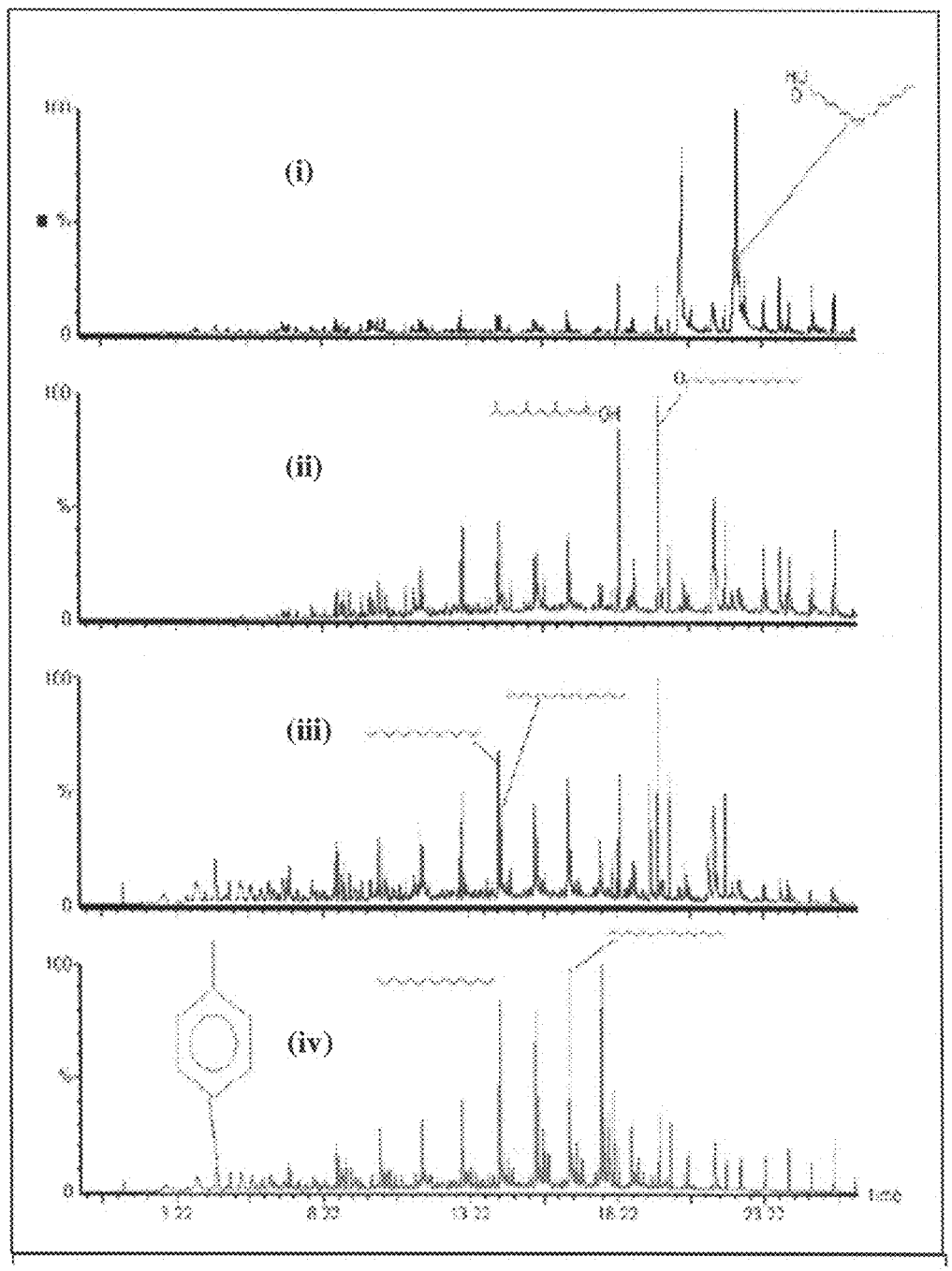
FIG. 39: Gas chromatograph of products resulting from thermal treatment of *Scenedesmus* sp. in the absence and presence of hydrogen. Some compounds are indicated in the figure to show progressive deoxygenation and hydrogenation of the bio-oil products with increasing treatment severity.
Figure 40:
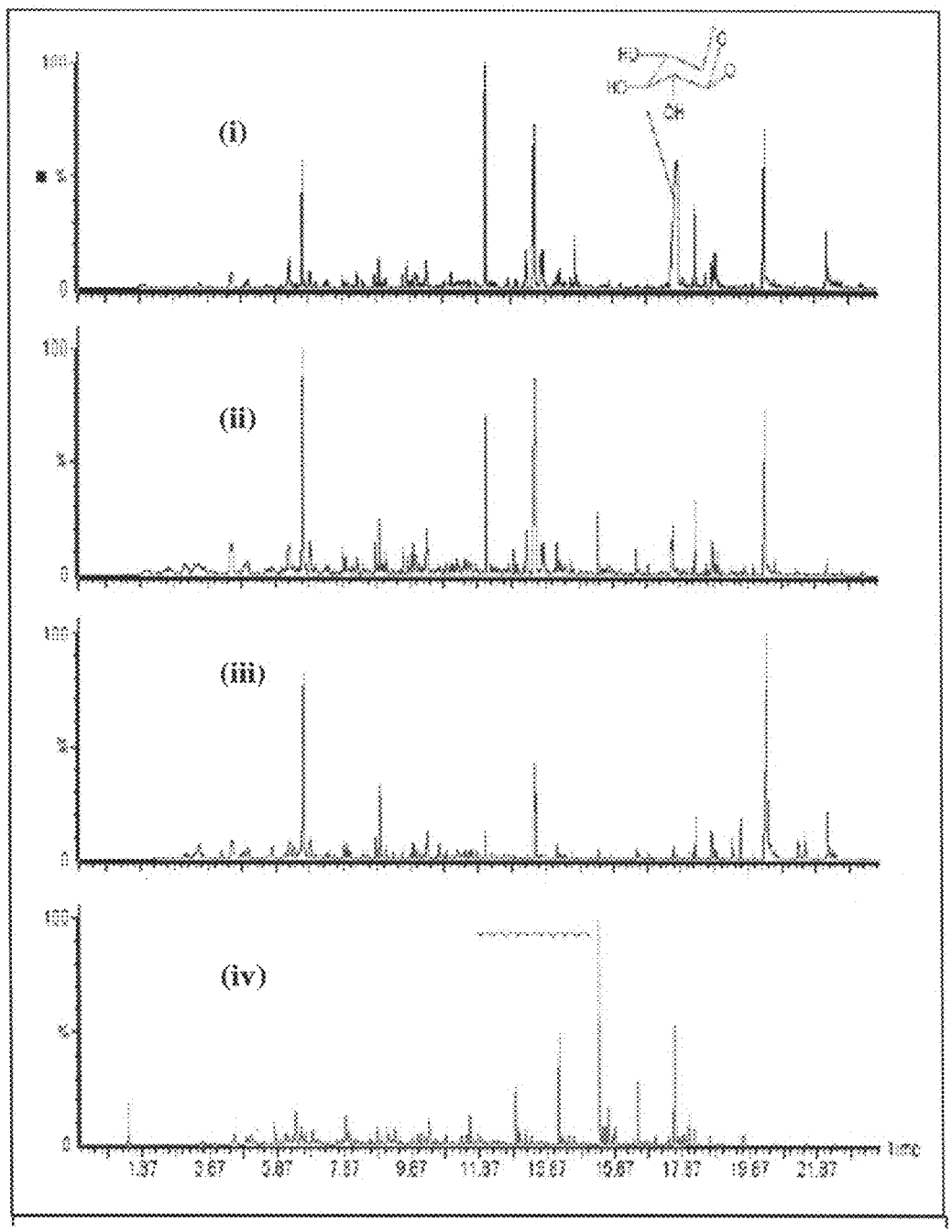
FIG. 40: Gas chromatograph of products resulting from thermal treatment of *Cladophora* sp. in the absence and presence of hydrogen. Some compounds are indicated in the figure to show progressive deoxygenation and hydrogenation of the bio-oil products with increasing treatment severity.

With each algal biomass type, products of pyrolysis alone (carried out in the absence of $H_2$, part (i) of FIGS. 38, 39, and 40), or pyrolysis in low pressure $H_2$ (part (ii) of FIGS. 38, 39, and 40), showed the presence of oxygenated compounds. When the experiments were performed under conditions conducive to catalytic hydrogenation (parts (iii) and (iv) of FIGS. 38, 39, and 40), straight chain hydrocarbons or aromatic compounds were produced and the oxygenated compounds were dramatically reduced. These results clearly show that bio-oils obtained by integrating thermal treatment of non-ligninaceous biomass (including algae) with catalytic hydrogenation result in hydrocarbon fuels similar to those derived from petroleum.

Example 11: Bio-Refinery Design

Figure 41:
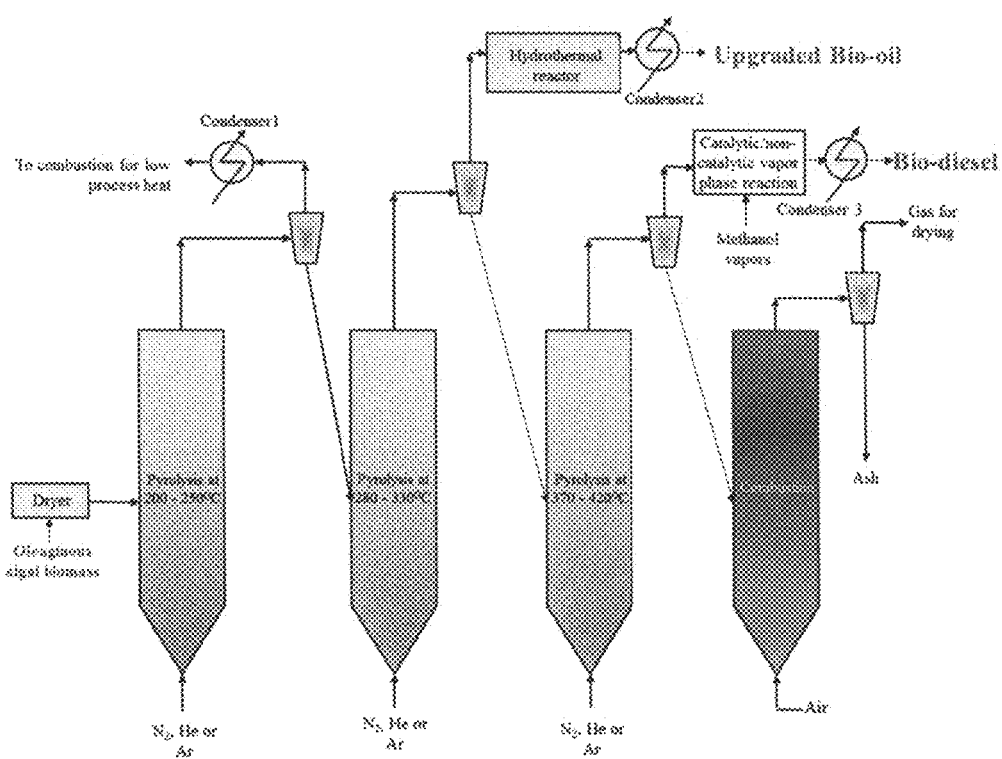
FIG. 41: Schematic illustration of a process design of a thermal fractionation process of a feedstock containing proteins, carbohydrates, and lipids. The process design shows strategies to recover multiple infrastructure-compatible fuels and co-products through an integrated process.

FIG. 41 shows a schematic illustration of a process design with three reactors (fixed or fluidized beds) each operating at the fractionation temperature of each of the three biopolymers—protein, carbohydrate, and lipid. The products from protein volatilization, rich in N-compounds, can be upgraded to fuel quality through hydrodenitrogenation followed by hydrogenation.

Alternatively, the crude bio-oil from this fraction can be combusted for process heat. High value N-compounds can also be recoverable from this fraction through downstream separation steps. Solids from the first reactor are shown to be pneumatically transported into the second reactor that operates at the volatilization temperature of carbohydrates. By integration with a hydrotreatment system, this reactor can directly produce an infrastructure-compatible green diesel or green gasoline. The lipid rich residue from this reactor can be volatilized to produce free fatty acids vapors in the third reactor. Vapor phase alcoholysis of the products from this reactor can result in the production of biodiesel—also compatible with existing infrastructure. The residue remaining at the end can be combusted to generate process heat or can be recovered as biochar for use as fertilizer/soil amendment.

Those skilled in the art will recognize that the bio-refinery design shown in FIG. 41 is readily adaptable to accommodate a two-step method of pyrolytic fractionation, as described in Examples 1-6.

Example 12: Non-Limiting Examples of Uses

The methods described herein are especially useful for the cost effective conversion of algal- and other non-ligninaceous biomass to infrastructure compatible liquid fuels. The methods are also especially useful in bio-refineries, petroleum industries, and biofuel manufacturers. The methods are therefore broadly useful for the production of liquid transportation fuels. As such, the size of the market for the methods described herein is immensely large.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

Citation of the any of the documents recited herein is not intended as an admission that any of the foregoing is pertinent prior art. All statements as to the date or representation as to the contents of these documents are based on the information available to the applicant and do not constitute any admission as to the correctness of the dates or contents of these documents.

What is claimed is:

1. A method of pyrolytic thermal fractionation of microalgae biomass comprising a protein component and a triglyceride component with or without an additional carbohydrate component, the method comprising:
   (a) heating the microalgae biomass to a first volatilization temperature of a first component comprising at least one of proteins or carbohydrates, and holding the first volatilization temperature of the heated microalgae biomass constant for a first period of time until no further mass loss of the first component occurs, thereby producing a first volatilized vapor product derived from proteins and/or carbohydrates, wherein the first volatilization temperature is in the range of from 180° C. to 360° C.;
   (b) removing and recovering the first volatilized vapor product from the microalgae biomass remaining from step (a);
   (c) heating the microalgae biomass remaining from step (b) to a second volatilization temperature of a second component comprising triglycerides, and holding the second volatilization temperature of the heated microalgae biomass constant for a second period of time until no further mass loss of the second component occurs, thereby producing a second volatilized vapor product derived from the triglycerides, wherein the second volatilization temperature is in the range of from 370° C. to 500° C.; and
   (d) removing and recovering the second volatilized vapor product from the microalgae biomass remaining from step (c).

2. The method of claim 1, wherein step (a) comprises simultaneously volatilizing proteins and carbohydrates.

3. The method of claim 1, wherein the second volatilized vapor product comprises one or more of: triglycerides, long chain fatty acids, di-glyceride, mono-glyceride, or hydrocarbons.

4. The method of claim 1, wherein the first volatilized vapor product comprises one or more of: organic acids, furans, N-compounds, water, aldehydes, ketones, or phenols.

5. The method of claim 1, wherein the first volatilization temperature is 320° C.

6. The method of claim 1, wherein the second volatilization temperature is 420° C.

7. The method of claim 1, wherein the microalgae biomass comprises *Chlorella* sp.

8. The method of claim 1, wherein the microalgae biomass comprises *Scenedesmus* sp.

9. The method of claim 1, wherein the first period of time is in the range of from 5 minutes to 30 minutes.

10. The method of claim 1, wherein the second period of time is in the range of from 5 minutes to 30 minutes.

11. The method of claim 1, wherein the first period of time is in the range of from 10 minutes to 15 minutes.

12. The method of claim 1, wherein the second period of time is in the range of from 10 minutes to 15 minutes.

13. The method of claim 1, further comprising combusting the first volatilized vapor product for recovery of process heat.

14. The method of claim 1, further comprising passing the first volatilized vapor product through hydro-denitrification and hydro-deoxygenation processes to reduce nitrogen and oxygen content of products.

15. The method of claim 1, further comprising subjecting the first volatilized vapor product to a downstream purification step to recover nitrogen- and/or oxygen-containing compounds.

16. The method of claim 1, further comprising esterifying the second volatilized vapor product to produce fatty acid alkyl esters or biodiesel.

17. The method of claim 16, wherein the esterification comprises gas-phase reactions with one or more alcohol vapors.

18. The method of claim 16, wherein the esterification is conducted with a solid or mineral acid catalyst.

19. The method of claim 16, wherein the esterification is conducted without a catalyst.

* * * * *